(12) United States Patent
Watson et al.

(10) Patent No.: US 8,082,110 B2
(45) Date of Patent: *Dec. 20, 2011

(54) LOW PERFUSION SIGNAL PROCESSING SYSTEMS AND METHODS

(75) Inventors: James Nicholas Watson, Dunfermline (GB); Paul Stanley Addison, Edinburgh (GB); Edward M. McKenna, Boulder, CO (US)

(73) Assignee: Nellcor Puritan Bennett Ireland, Mervue Galway (IE)

( * ) Notice: Subject to any disclaimer, the term of this patent is extended or adjusted under 35 U.S.C. 154(b) by 413 days.

This patent is subject to a terminal disclaimer.

(21) Appl. No.: 12/249,325

(22) Filed: Oct. 10, 2008

(65) Prior Publication Data

US 2010/0017142 A1    Jan. 21, 2010

Related U.S. Application Data

(60) Provisional application No. 61/080,977, filed on Jul. 15, 2008.

(51) Int. Cl.
*G01N 33/48* (2006.01)
(52) U.S. Cl. .......................................................... 702/19
(58) Field of Classification Search ...................... 702/19
See application file for complete search history.

(56) References Cited

U.S. PATENT DOCUMENTS

| | | | |
|---|---|---|---|
| 4,289,141 A | 9/1981 | Cormier | |
| 5,439,483 A | 8/1995 | Duong-Van | |
| 5,590,650 A | 1/1997 | Genova | |
| 5,632,272 A | 5/1997 | Diab et al. | |
| 5,778,881 A | 7/1998 | Sun et al. | |
| 5,795,304 A | 8/1998 | Sun et al. | |
| 5,797,840 A | 8/1998 | Akselrod | |
| 5,827,195 A | 10/1998 | Lander | |
| 5,967,995 A | 10/1999 | Shusterman et al. | |
| 6,002,952 A | 12/1999 | Diab et al. | |
| 6,036,653 A | 3/2000 | Baba et al. | |
| 6,094,592 A | 7/2000 | Yorkey | |
| 6,095,984 A | 8/2000 | Amano et al. | |
| 6,117,075 A | 9/2000 | Barnea | |
| 6,129,675 A | 10/2000 | Jay | |
| 6,135,966 A | 10/2000 | Ko | |
| 6,171,257 B1 | 1/2001 | Weil et al. | |

(Continued)

FOREIGN PATENT DOCUMENTS

JP    09-084776    3/1997

(Continued)

OTHER PUBLICATIONS

Paul S Addison, Wavelet transforms and the ECG: a review, Institute of Physics Publishing Physiological Measurement, Physiol. Meas. 26 (2005) R155-R199, doi:10.1088/0967-3334/26/5/R01, 2005 IOP Publishing Ltd Printed in the UK, p. R155-R199.*

(Continued)

*Primary Examiner* — Tung S Lau

(57) ABSTRACT

In some embodiments, systems and methods for identifying a low perfusion condition are provided by transforming a signal using a wavelet transform to generate a scalogram. A pulse band and adjacent marker regions in the scalogram are identified. Characteristics of the marker regions are used to detect the existence of a lower perfusion condition. If such a condition is detected, an event may be triggered, such as an alert or notification.

11 Claims, 14 Drawing Sheets
(1 of 14 Drawing Sheet(s) Filed in Color)

U.S. PATENT DOCUMENTS

| | | |
|---|---|---|
| 6,171,258 B1 | 1/2001 | Karakasoglu et al. |
| 6,208,951 B1 | 3/2001 | Kumar et al. |
| 6,293,915 B1 | 9/2001 | Amano et al. |
| 6,325,761 B1 | 12/2001 | Jay |
| 6,361,501 B1 | 3/2002 | Amano et al. |
| 6,393,311 B1 | 5/2002 | Edgar, Jr. et al. |
| 6,434,408 B1 | 8/2002 | Heckel |
| 6,561,986 B2 | 5/2003 | Baura |
| 6,566,251 B2 | 5/2003 | Allen et al. |
| 6,584,336 B1 | 6/2003 | Ali et al. |
| 6,608,934 B2 | 8/2003 | Scheirer |
| 6,654,623 B1 | 11/2003 | Kastle |
| 6,654,624 B2 | 11/2003 | Diab et al. |
| 6,810,277 B2 | 10/2004 | Edgar, Jr. et al. |
| 6,931,269 B2 | 8/2005 | Terry |
| 7,001,337 B2 | 2/2006 | Dekker |
| 7,020,507 B2 | 3/2006 | Scharf |
| 7,035,679 B2 | 4/2006 | Addison |
| 7,043,293 B1 | 5/2006 | Baura |
| 7,054,453 B2 | 5/2006 | Causevic |
| 7,054,454 B2 | 5/2006 | Causevic et al. |
| 7,079,888 B2 | 7/2006 | Oung |
| 7,171,269 B1 | 1/2007 | Addison |
| 7,173,525 B2 | 2/2007 | Albert |
| 7,203,267 B2 | 4/2007 | De Man et al. |
| 7,225,013 B2 | 5/2007 | Geva et al. |
| 7,254,500 B2 | 8/2007 | Makeig |
| 7,289,835 B2 | 10/2007 | Mansfield |
| 7,471,969 B2 | 12/2008 | Diab et al. |
| 7,515,949 B2 | 4/2009 | Norris |
| 7,519,488 B2 | 4/2009 | Fu |
| 7,523,011 B2 | 4/2009 | Akiyama et al. |
| 2003/0163057 A1 | 8/2003 | Flick et al. |
| 2004/0158134 A1 | 8/2004 | Diab et al. |
| 2005/0043616 A1 | 2/2005 | Chinchoy |
| 2005/0209516 A1 | 9/2005 | Fraden |
| 2006/0206019 A1 | 9/2006 | Zhang et al. |
| 2006/0209631 A1 | 9/2006 | Melese et al. |
| 2006/0211930 A1 | 9/2006 | Scharf et al. |
| 2006/0229519 A1 | 10/2006 | Fujiwara et al. |
| 2006/0258921 A1 | 11/2006 | Addison et al. |
| 2006/0265022 A1 | 11/2006 | John et al. |
| 2007/0021673 A1 | 1/2007 | Arbel et al. |
| 2007/0073120 A1 | 3/2007 | Li et al. |
| 2007/0073124 A1 | 3/2007 | Li et al. |
| 2007/0149872 A1 | 6/2007 | Zhang et al. |
| 2007/0167694 A1 | 7/2007 | Causevic et al. |
| 2007/0167851 A1 | 7/2007 | Vitali et al. |
| 2007/0282212 A1 | 12/2007 | Sierra et al. |
| 2008/0045832 A1 | 2/2008 | McGrath |
| 2008/0082018 A1 | 4/2008 | Sackner et al. |
| 2008/0214903 A1 | 9/2008 | Orbach |
| 2008/0243021 A1 | 10/2008 | Causevic et al. |
| 2010/0016691 A1* | 1/2010 | Watson et al. ............... 600/323 |

FOREIGN PATENT DOCUMENTS

| | | |
|---|---|---|
| WO | WO 01/025802 | 4/2001 |
| WO | WO 01/062152 | 8/2001 |
| WO | 03/055395 A | 7/2003 |
| WO | WO 03/055395 | 7/2003 |
| WO | 2004/075746 A | 9/2004 |
| WO | WO 2004/105601 | 12/2004 |
| WO | WO 2005/096170 | 10/2005 |
| WO | WO 2006/085120 | 8/2006 |
| WO | 2008/020845 A | 2/2008 |

OTHER PUBLICATIONS

Addison, Paul S., The Illustrated Wavelet Transform Handbook, Taylor & Francis Group, 2002.

Addison, Paul, "The Little Wave with the Big Future," Physics World, Mar. 2004, pp. 35-39.

Clifton, David, Douglas, J. Graham, Addison, Paul S., Watson, James N., "Measurement of Respiratory Rate from the Photoplethysmogram in Chest Clinic Patients," Journal of Clinical Monitoring and Computing, 2006.

Leonard, Paul A., Douglas, J. Graham, Grubb, Neil R., Clifton, David, Addison, Paul S., Watson, James N., "A Fully Automated Algorithm for the Determination of Respiratory Rate From the Photoplethysmogram," Journal of Clinical Monitoring and Computing, 2006.

Leonard, Paul A., Clifton, David, Addison, Paul S., Watson, James N., Beattie, Tom "An Automated Algorithm for Determining Respiratory Rate by Photoplethysmogram in Children," Acta Paediatricia, 2006; 95: 1124-1128.

Legarreta, I. Romero, Addison, P. S., Reed, M. J., Grubb, N. Clegg, G. R., Robertson, C. E., Watson, J. N., "Continuous Wavelet Transform Modulus Maxima Analysis of the Electrocardiogram: Beat Characterisation and Beat-to-Beat Measurement," International Journal of Wavelets, Multiresolution and Information Processing, vol. 3, No. 1, 2004, pp. 1-24.

Yamada, Michio, "Wavelet Analysis and Its Application," Journal of the Institute of Electronics, Information and Communication Engineers, vol. 76, No. 5, May 1993, pp. 518-528.

* cited by examiner

LOW PERFUSION SIGNAL PROCESSING SYSTEMS AND METHODS

CROSS REFERENCE TO RELATED APPLICATION

This application claims the benefit of U.S. Provisional Application No. 61/080,977, filed Jul. 15, 2008 which is hereby incorporated by reference herein in its entirety.

SUMMARY

The present disclosure relates to signal processing and, more particularly, the present disclosure relates to using continuous wavelet transforms for processing, for example, a photoplethysmograph (PPG) signal. PPG signals are used in a variety of fields, including in medical monitoring devices, such as a pulse oximeter. A pulse oximeter is a device that is capable of indirectly measuring blood oxygen saturation and is typically used by healthcare providers as a monitoring device for patients. The oximeter generally uses a light emitter that shines through a monitoring site or point on a patient. A photodetector or other sensor may be used to receive the light that has passed through the monitoring site. The light passing through the site may be measured and analyzed to determine the patient's blood oxygen saturation using, for example, a scalogram generated by wavelet-transformation of the PPG signal.

Since oxygen is critical to sustain human life, monitoring patients' blood oxygen saturation is one important indicator of a patient's physiological condition. If blood oxygen saturation levels determined by the oximeter are low, out of range, above or below a certain threshold, this may be an indication that the patient is generally experiencing low perfusion, high vascular peripheral resistance, or other condition, or that the monitoring site is locally experiencing low perfusion, high vascular peripheral resistance, or other condition. Certain illnesses or physiological conditions may cause low perfusion, and high peripheral resistance. Low perfusion may also be caused (or worsened) by patient position, or external factors.

In the various embodiments disclosed herein, features of a PPG scalogram are analyzed to determine whether the monitored patient is experiencing low perfusion or high vascular peripheral resistance. When low perfusion or high vascular peripheral resistance is detected, a corrective action may be triggered. The corrective action may include an alert to examine the patient, reposition a sensor, use a second sensor, or other action.

One way to perform the analysis may include identifying features of the scalogram, for example, marker regions, and residual markers located near a pulse band. Another technique may be provided by comparing features of the scalogram against, for example, selectable thresholds, other scalograms having known and distinct aspects and features, or other comparative elements. These techniques are further described herein. Although the embodiments herein are discussed in reference to use with a pulse oximeter, they are equally applicable to other types of devices, including continuous non-invasive blood pressure (CNIBP) measurement devices. Systems and methods for calculating CNIBP are described in Chen et al. U.S. Pat. No. 6,566,251 and Sethi et al. U.S. patent application Ser. No. 12/242,238, entitled "SYSTEMS AND METHODS FOR NON-INVASIVE BLOOD PRESSURE MONITORING," filed Sep. 30, 2008, both of which are incorporated by reference herein in their entireties.

An embodiment is provided by a method comprising receiving a signal that may be transformed using a wavelet transform. The transformed signal may be used to generate a scalogram. A pulse band and a marker region adjacent to the pulse band in the scalogram may be identified. A characteristic of the marker region may be identified and used as a basis for determining that a low perfusion condition exists. If such condition exists, an event may trigger. The marker region may be identified using ridges or modulus maxima of the scalogram. Some characteristics of the marker region include: a change in energy within the marker region over time, a change in amplitude within the marker region over time, a residual marker, a number of residual markers, a size of the residual marker, a location of the residual marker, energy of the residual marker, amplitude of the residual marker, and strength of the residual marker. The characteristics may be compared with a threshold, which may cause the event to trigger. The threshold may be based in part on a user classification. The user classification may also be used as a basis for triggering the event. Some types of events include: sending a control signal to a display, sending a control signal to a speaker, generating an alert, sending a control signal to a second sensor, and moving a sensor. Some examples of alerts include: an indication of a low perfusion condition, an indication to examine a patient, an indication to move the sensor, an indication to move the sensor closer to an artery, an indication to move the sensor away from an artery, and an indication of use of a second sensor. In some embodiments, a second scalogram may be generated and compared against the original scalogram.

In another embodiment, a system is provided comprising: a signal generator for generating a signal, a processor coupled to the signal generator, and a display. The processor is capable of transforming the signal using a wavelet transform. The transformed signal may be used as a basis for generating a scalogram. A pulse band and marker region adjacent to the pulse band in the scalogram may be identified by the processor. The processor is also capable of identifying a characteristic of the marker region, which may be used for determining that a low perfusion condition exists. The processor may also trigger an event.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other features of the present disclosure, its nature and various advantages will be more apparent upon consideration of the following detailed description, taken in conjunction with the accompanying drawings in which.

DETAILED DESCRIPTION

Figure 1:
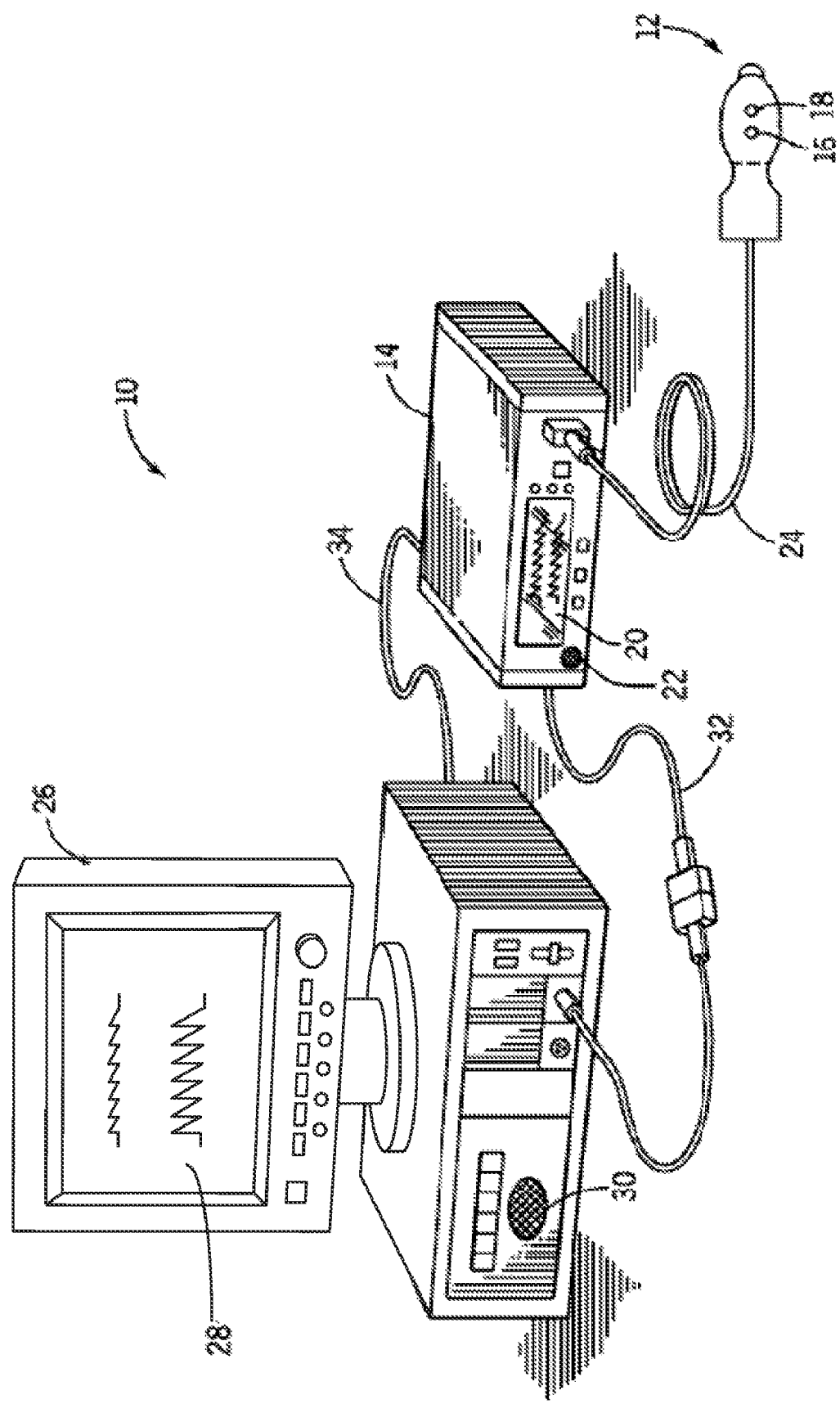
FIG. 1 shows an illustrative pulse oximetry system in accordance with an embodiment.

In medicine, a plethysmograph is an instrument that measures physiological parameters, such as variations in the size of an organ or body part, through an analysis of the blood passing through or present in the targeted body part, or a depiction of these variations. An oximeter is an instrument that may determine the oxygen saturation of the blood. One common type of oximeter is a pulse oximeter, which determines oxygen saturation by analysis of an optically sensed plethysmograph.

A pulse oximeter is a medical device that may indirectly measure the oxygen saturation of a patient's blood (as opposed to measuring oxygen saturation directly by analyzing a blood sample taken from the patient) and changes in blood volume in the skin. Ancillary to the blood oxygen saturation measurement, pulse oximeters may also be used to measure the pulse rate of the patient. Pulse oximeters typically measure and display various blood flow characteristics including, but not limited to, the oxygen saturation of hemoglobin in arterial blood.

An oximeter may include a light sensor that is placed at a site on a patient, typically a fingertip, toe, forehead or earlobe, or in the case of a neonate, across a foot. The oximeter may pass light using a light source through blood perfused tissue and photoelectrically sense the absorption of light in the tissue. For example, the oximeter may measure the intensity of light that is received at the light sensor as a function of time. A signal representing light intensity versus time or a mathematical manipulation of this signal (e.g., a scaled version thereof, a log taken thereof, a scaled version of a log taken thereof, etc.) may be referred to as the photoplethysmograph (PPG) signal. In addition, the term "PPG signal," as used herein, may also refer to an absorption signal (i.e., representing the amount of light absorbed by the tissue) or any suitable mathematical manipulation thereof. The light intensity or the amount of light absorbed may then be used to calculate the amount of the blood constituent (e.g., oxyhemoglobin) being measured as well as the pulse rate and when each individual pulse occurs.

The light passed through the tissue is selected to be of one or more wavelengths that are absorbed by the blood in an amount representative of the amount of the blood constituent present in the blood. The amount of light passed through the tissue varies in accordance with the changing amount of blood constituent in the tissue and the related light absorption. Red and infrared wavelengths may be used because it has been observed that highly oxygenated blood will absorb relatively less red light and more infrared light than blood with a lower oxygen saturation. By comparing the intensities of two wavelengths at different points in the pulse cycle, it is possible to estimate the blood oxygen saturation of hemoglobin in arterial blood.

When the measured blood parameter is the oxygen saturation of hemoglobin, a convenient starting point assumes a saturation calculation based on Lambert-Beer's law. The following notation will be used herein:

$$I(\lambda,t)=I_o(\lambda)\exp(-(s\beta_o(\lambda)+(1-s)\beta_r(\lambda))l(t)) \quad (1)$$

where:
$\lambda$=wavelength;
t=time;
I=intensity of light detected;
$I_o$=intensity of light transmitted;
s=oxygen saturation;
$\beta_o$, $\beta_r$=empirically derived absorption coefficients; and
l(t)=a combination of concentration and path length from emitter to detector as a function of time.

The traditional approach measures light absorption at two wavelengths (e.g., red and infrared (IR)), and then calculates saturation by solving for the "ratio of ratios" as follows.

1. First, the natural logarithm of (1) is taken ("log" will be used to represent the natural logarithm) for IR and Red $$\log I = \log I_o - (s\beta_o + (1-s)\beta_r)l \quad (2)$$

2. (2) is then differentiated with respect to time $$\frac{d\log I}{dt} = -(s\beta_o + (1-s)\beta_r)\frac{dl}{dt} \quad (3)$$

3. Red (3) is divided by IR (3)

$$\frac{d\log I(\lambda_R)/dt}{d\log I(\lambda_{IR})/dt} = \frac{s\beta_o(\lambda_R)+(1-s)\beta_r(\lambda_R)}{s\beta_o(\lambda_{IR})+(1-s)\beta_r(\lambda_{IR})} \quad (4)$$

4. Solving for s $$s = \frac{\frac{d\log I(\lambda_{IR})}{dt}\beta_r(\lambda_R) - \frac{d\log I(\lambda_R)}{dt}\beta_r(\lambda_{IR})}{\frac{d\log I(\lambda_R)}{dt}(\beta_o(\lambda_{IR})-\beta_r(\lambda_{IR})) - \frac{d\log I(\lambda_{IR})}{dt}(\beta_o(\lambda_R)-\beta_r(\lambda_R))}$$

Note in discrete time $$\frac{d\log I(\lambda,t)}{dt} \simeq \log I(\lambda,t_2) - \log I(\lambda,t_1)$$

Using log A−log B=log A/B, $$\frac{d\log I(\lambda,t)}{dt} \simeq \log\left(\frac{I(t_2,\lambda)}{I(t_1,\lambda)}\right)$$

So, (4) can be rewritten as $$\frac{\frac{d\log I(\lambda_R)}{dt}}{\frac{d\log I(\lambda_{IR})}{dt}} \simeq \frac{\log\left(\frac{I(t_1,\lambda_R)}{I(t_2,\lambda_R)}\right)}{\log\left(\frac{I(t_1,\lambda_{IR})}{I(t_2,\lambda_{IR})}\right)} = R \quad (5)$$

where R represents the "ratio of ratios." Solving (4) for s using (5) gives $$s = \frac{\beta_r(\lambda_R) - R\beta_r(\lambda_{IR})}{R(\beta_o(\lambda_{IR}) - \beta_r(\lambda_{IR})) - \beta_o(\lambda_R) + \beta_r(\lambda_R)}.$$

From (5), R can be calculated using two points (e.g., PPG maximum and minimum), or a family of points. One method using a family of points uses a modified version of (5). Using the relationship $$\frac{d\log I}{dt} = \frac{dI/dt}{I} \quad (6)$$

now (5) becomes $$\frac{\frac{d\log I(\lambda_R)}{dt}}{\frac{d\log I(\lambda_{IR})}{dt}} \simeq \frac{\frac{I(t_2,\lambda_R) - I(t_1,\lambda_R)}{I(t_1,\lambda_R)}}{\frac{I(t_2,\lambda_{IR}) - I(t_1,\lambda_{IR})}{I(t_1,\lambda_{IR})}} \quad (7)$$
$$= \frac{[I(t_2,\lambda_R) - I(t_1,\lambda_R)]I(t_1,\lambda_{IR})}{[I(t_2,\lambda_{IR}) - I(t_1,\lambda_{IR})]I(t_1,\lambda_R)}$$
$$= R$$

which defines a cluster of points whose slope of y versus x will give R where $$x(t) = [I(t_2,\lambda_{IR}) - I(t_1,\lambda_{IR})]I(t_1,\lambda_R)$$

$$y(t) = [I(t_2,\lambda_R) - I(t_1,\lambda_R)]I(t_1,\lambda_{IR})$$

$$y(t) = Rx(t) \quad (8)$$

FIG. 1 is a perspective view of an embodiment of a pulse oximetry system 10. System 10 may include a sensor 12 and a pulse oximetry monitor 14. Sensor 12 may include an emitter 16 for emitting light at two or more wavelengths into a patient's tissue. A detector 18 may also be provided in sensor 12 for detecting the light originally from emitter 16 that emanates from the patient's tissue after passing through the tissue.

According to another embodiment and as will be described, system 10 may include a plurality of sensors forming a sensor array in lieu of single sensor 12. Each of the sensors of the sensor array may be a complementary metal oxide semiconductor (CMOS) sensor. Alternatively, each sensor of the array may be charged coupled device (CCD) sensor. In another embodiment, the sensor array may be made up of a combination of CMOS and CCD sensors. The CCD sensor may comprise a photoactive region and a transmission region for receiving and transmitting data whereas the CMOS sensor may be made up of an integrated circuit having an array of pixel sensors. Each pixel may have a photodetector and an active amplifier.

According to an embodiment, emitter 16 and detector 18 may be on opposite sides of a digit such as a finger or toe, in which case the light that is emanating from the tissue has passed completely through the digit. In an embodiment, emitter 16 and detector 18 may be arranged so that light from emitter 16 penetrates the tissue and is reflected by the tissue into detector 18, such as a sensor designed to obtain pulse oximetry data from a patient's forehead.

In an embodiment, the sensor or sensor array may be connected to and draw its power from monitor 14 as shown. In another embodiment, the sensor may be wirelessly connected to monitor 14 and include its own battery or similar power supply (not shown). Monitor 14 may be configured to calculate physiological parameters based at least in part on data received from sensor 12 relating to light emission and detection. In an alternative embodiment, the calculations may be performed on the monitoring device itself and the result of the oximetry reading may be passed to monitor 14. Further, monitor 14 may include a display 20 configured to display the physiological parameters or other information about the system. In the embodiment shown, monitor 14 may also include a speaker 22 to provide an audible sound that may be used in various other embodiments, such as for example, sounding an audible alarm in the event that a patient's physiological parameters are not within a predefined normal range.

In an embodiment, sensor 12, or the sensor array, may be communicatively coupled to monitor 14 via a cable 24. However, in other embodiments, a wireless transmission device (not shown) or the like may be used instead of or in addition to cable 24.

In the illustrated embodiment, pulse oximetry system 10 may also include a multi-parameter patient monitor 26. The monitor may be cathode ray tube type, a flat panel display (as shown) such as a liquid crystal display (LCD) or a plasma display, or any other type of monitor now known or later developed. Multi-parameter patient monitor 26 may be configured to calculate physiological parameters and to provide a display 28 for information from monitor 14 and from other medical monitoring devices or systems (not shown). For example, multiparameter patient monitor 26 may be configured to display an estimate of a patient's blood oxygen saturation generated by pulse oximetry monitor 14 (referred to as an "SpO$_2$" measurement), pulse rate information from monitor 14 and blood pressure from a blood pressure monitor (not shown) on display 28.

Monitor 14 may be communicatively coupled to multi-parameter patient monitor 26 via a cable 32 or 34 that is coupled to a sensor input port or a digital communications port, respectively and/or may communicate wirelessly (not shown). In addition, monitor 14 and/or multi-parameter patient monitor 26 may be coupled to a network to enable the sharing of information with servers or other workstations (not shown). Monitor 14 may be powered by a battery (not shown) or by a conventional power source such as a wall outlet.

Figure 2:
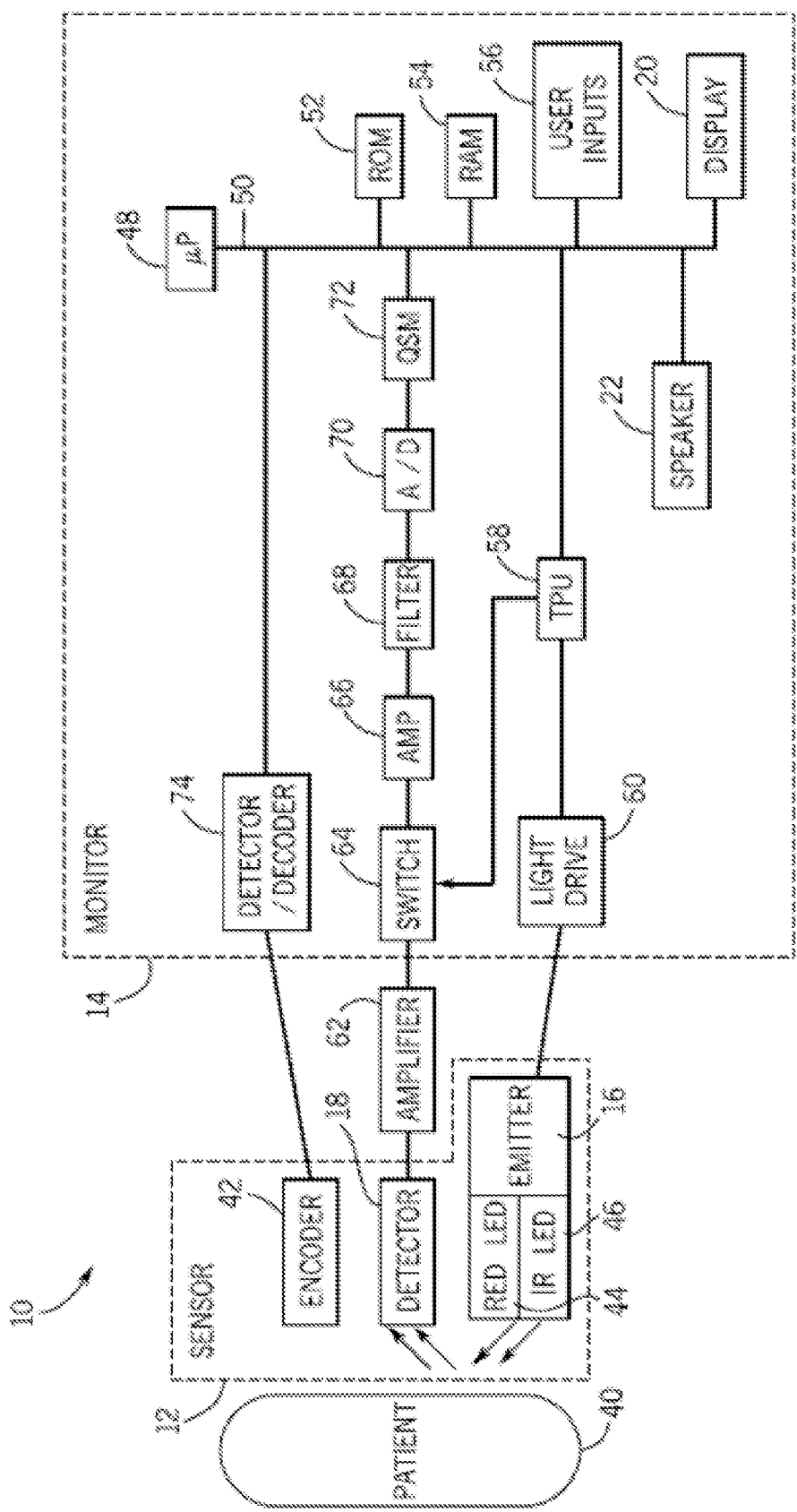
FIG. 2 is a block diagram of the illustrative pulse oximetry system of FIG. 1 coupled to a patient in accordance with an embodiment.

FIG. 2 is a block diagram of a pulse oximetry system, such as pulse oximetry system 10 of FIG. 1, which may be coupled to a patient 40 in accordance with an embodiment. Certain illustrative components of sensor 12 and monitor 14 are illustrated in FIG. 2. Sensor 12 may include emitter 16, detector 18, and encoder 42. In the embodiment shown, emitter 16 may be configured to emit at least two wavelengths of light (e.g., RED and IR) into a patient's tissue 40. Hence, emitter 16 may include a RED light emitting light source such as RED light emitting diode (LED) 44 and an IR light emitting light source such as IR LED 46 for emitting light into the patient's tissue 40 at the wavelengths used to calculate the patient's physiological parameters. In one embodiment, the RED wavelength may be between about 600 nm and about 700 nm, and the IR wavelength may be between about 800 nm and about 1000 nm. In embodiments where a sensor array is used in place of single sensor, each sensor may be configured to emit a single wavelength. For example, a first sensor emits only a RED light while a second only emits an IR light.

It will be understood that, as used herein, the term "light" may refer to energy produced by radiative sources and may include one or more of ultrasound, radio, microwave, millimeter wave, infrared, visible, ultraviolet, gamma ray or X-ray electromagnetic radiation. As used herein, light may also include any wavelength within the radio, microwave, infrared, visible, ultraviolet, or X-ray spectra, and that any suitable wavelength of electromagnetic radiation may be appropriate for use with the present techniques. Detector 18 may be chosen to be specifically sensitive to the chosen targeted energy spectrum of the emitter 16.

In an embodiment, detector 18 may be configured to detect the intensity of light at the RED and IR wavelengths. Alternatively, each sensor in the array may be configured to detect an intensity of a single wavelength. In operation, light may enter detector 18 after passing through the patient's tissue 40. Detector 18 may convert the intensity of the received light into an electrical signal. The light intensity is directly related to the absorbance and/or reflectance of light in the tissue 40. That is, when more light at a certain wavelength is absorbed or reflected, less light of that wavelength is received from the tissue by the detector 18. After converting the received light to an electrical signal, detector 18 may send the signal to monitor 14, where physiological parameters may be calculated based on the absorption of the RED and IR wavelengths in the patient's tissue 40.

In an embodiment, encoder 42 may contain information about sensor 12, such as what type of sensor it is (e.g., whether the sensor is intended for placement on a forehead or digit) and the wavelengths of light emitted by emitter 16. This information may be used by monitor 14 to select appropriate algorithms, lookup tables and/or calibration coefficients stored in monitor 14 for calculating the patient's physiological parameters.

Encoder 42 may contain information specific to patient 40, such as, for example, the patient's age, weight, and diagnosis. This information may allow monitor 14 to determine, for example, patient-specific threshold ranges in which the patient's physiological parameter measurements should fall and to enable or disable additional physiological parameter algorithms. Encoder 42 may, for instance, be a coded resistor which stores values corresponding to the type of sensor 12 or the type of each sensor in the sensor array, the wavelengths of light emitted by emitter 16 on each sensor of the sensor array, and/or the patient's characteristics. In another embodiment, encoder 42 may include a memory on which one or more of the following information may be stored for communication to monitor 14: the type of the sensor 12; the wavelengths of light emitted by emitter 16; the particular wavelength each sensor in the sensor array is monitoring; a signal threshold for each sensor in the sensor array; any other suitable information; or any combination thereof.

In an embodiment, signals from detector 18 and encoder 42 may be transmitted to monitor 14. In the embodiment shown, monitor 14 may include a general-purpose microprocessor 48 connected to an internal bus 50. Microprocessor 48 may be adapted to execute software, which may include an operating system and one or more applications, as part of performing the functions described herein. Also connected to bus 50 may be a read-only memory (ROM) 52, a random access memory (RAM) 54, user inputs 56, display 20, and speaker 22.

RAM 54 and ROM 52 are illustrated by way of example, and not limitation. Any suitable computer-readable media may be used in the system for data storage. Computer-readable media are capable of storing information that can be interpreted by microprocessor 48. This information may be data or may take the form of computer-executable instructions, such as software applications, that cause the microprocessor to perform certain functions and/or computer-implemented methods. Depending on the embodiment, such computer-readable media may include computer storage media and communication media. Computer storage media may include volatile and non-volatile, removable and non-removable media implemented in any method or technology for storage of information such as computer-readable instructions, data structures, program modules or other data. Computer storage media may include, but is not limited to, RAM, ROM, EPROM, EEPROM, flash memory or other solid state memory technology, CD-ROM, DVD, or other optical storage, magnetic cassettes, magnetic tape, magnetic disk storage or other magnetic storage devices, or any other medium which can be used to store the desired information and which can be accessed by components of the system.

In the embodiment shown, a time processing unit (TPU) 58 may provide timing control signals to a light drive circuitry 60, which may control when emitter 16 is illuminated and multiplexed timing for the RED LED 44 and the IR LED 46. TPU 58 may also control the gating-in of signals from detector 18 through an amplifier 62 and a switching circuit 64. These signals are sampled at the proper time, depending upon which light source is illuminated. The received signal from detector 18 may be passed through an amplifier 66, a low pass filter 68, and an analog-to-digital converter 70. The digital data may then be stored in a queued serial module (QSM) 72 (or buffer) for later downloading to RAM 54 as QSM 72 fills up. In one embodiment, there may be multiple separate parallel paths having amplifier 66, filter 68, and A/D converter 70 for multiple light wavelengths or spectra received.

In an embodiment, microprocessor 48 may determine the patient's physiological parameters, such as $SpO_2$ and pulse rate, using various algorithms and/or look-up tables based on the value of the received signals and/or data corresponding to the light received by detector 18. Signals corresponding to information about patient 40, and particularly about the intensity of light emanating from a patient's tissue over time, may be transmitted from encoder 42 to a decoder 74. These signals may include, for example, encoded information relating to patient characteristics. Decoder 74 may translate these signals to enable the microprocessor to determine the thresholds based on algorithms or look-up tables stored in ROM 52. User inputs 56 may be used to enter information about the patient, such as age, weight, height, diagnosis, medications, treatments, and so forth. In an embodiment, display 20 may exhibit a list of values which may generally apply to the patient, such as, for example, age ranges or medication families, which the user may select using user inputs 56.

The optical signal through the tissue can be degraded by noise, among other sources. One source of noise is ambient light that reaches the light detector. Another source of noise is electromagnetic coupling from other electronic instruments. Movement of the patient also introduces noise and affects the signal. For example, the contact between the detector and the skin, or the emitter and the skin, can be temporarily disrupted when movement causes either to move away from the skin. In addition, because blood is a fluid, it responds differently than the surrounding tissue to inertial effects, thus resulting in momentary changes in volume at the point to which the oximeter probe is attached.

Noise (e.g., from patient movement) can degrade a pulse oximetry signal relied upon by a physician, without the physician's awareness. This is especially true if the monitoring of the patient is remote, the motion is too small to be observed, or the doctor is watching the instrument or other parts of the patient, and not the sensor site. Processing pulse oximetry (i.e., PPG) signals may involve operations that reduce the amount of noise present in the signals or otherwise identify noise components in order to prevent them from affecting measurements of physiological parameters derived from the PPG signals.

It will be understood that the present disclosure is applicable to any suitable signals and that PPG signals are used merely for illustrative purposes. Those skilled in the art will recognize that the present disclosure has wide applicability to other signals including, but not limited to other biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In one embodiment, a PPG signal may be transformed using a continuous wavelet transform. Information derived from the transform of the PPG signal (i.e., in wavelet space) may be used to provide measurements of one or more physiological parameters.

The continuous wavelet transform of a signal x(t) in accordance with the present disclosure may be defined as $$T(a, b) = \frac{1}{\sqrt{a}} \int_{-\infty}^{+\infty} x(t) \psi^* \left( \frac{t-b}{a} \right) dt \qquad (9)$$

where $\psi^*(t)$ is the complex conjugate of the wavelet function $\psi(t)$, a is the dilation parameter of the wavelet and b is the location parameter of the wavelet. The transform given by equation (9) may be used to construct a representation of a signal on a transform surface. The transform may be regarded as a time-scale representation. Wavelets are composed of a range of frequencies, one of which may be denoted as the characteristic frequency of the wavelet, where the characteristic frequency associated with the wavelet is inversely proportional to the scale a. One example of a characteristic frequency is the dominant frequency. Each scale of a particular wavelet may have a different characteristic frequency. The underlying mathematical detail required for the implementation within a time-scale can be found, for example, in Paul S. Addison, The Illustrated Wavelet Transform Handbook (Taylor & Francis Group 2002), which is hereby incorporated by reference herein in its entirety.

The continuous wavelet transform decomposes a signal using wavelets, which are generally highly localized in time. The continuous wavelet transform may provide a higher resolution relative to discrete transforms, thus providing the ability to garner more information from signals than typical frequency transforms such as Fourier transforms (or any other spectral techniques) or discrete wavelet transforms. Continuous wavelet transforms allow for the use of a range of wavelets with scales spanning the scales of interest of a signal such that small scale signal components correlate well with the smaller scale wavelets and thus manifest at high energies at smaller scales in the transform. Likewise, large scale signal components correlate well with the larger scale wavelets and thus manifest at high energies at larger scales in the transform. Thus, components at different scales may be separated and extracted in the wavelet transform domain. Moreover, the use of a continuous range of wavelets in scale and time position allows for a higher resolution transform than is possible relative to discrete techniques.

In addition, transforms and operations that convert a signal or any other type of data into a spectral (i.e., frequency) domain necessarily create a series of frequency transform values in a two-dimensional coordinate system where the two dimensions may be frequency and, for example, amplitude. For example, any type of Fourier transform would generate such a two-dimensional spectrum. In contrast, wavelet transforms, such as continuous wavelet transforms, are required to be defined in a three-dimensional coordinate system and generate a surface with dimensions of time, scale and, for example, amplitude. Hence, operations performed in a spectral domain cannot be performed in the wavelet domain; instead the wavelet surface must be transformed into a spectrum (i.e., by performing an inverse wavelet transform to convert the wavelet surface into the time domain and then performing a spectral transform from the time domain). Conversely, operations performed in the wavelet domain cannot be performed in the spectral domain; instead a spectrum must first be transformed into a wavelet surface (i.e., by performing an inverse spectral transform to convert the spectral domain into the time domain and then performing a wavelet transform from the time domain). Nor does a cross-section of the three-dimensional wavelet surface along, for example, a particular point in time equate to a frequency spectrum upon which spectral-based techniques may be used. At least because wavelet space includes a time dimension, spectral techniques and wavelet techniques are not interchangeable. It will be understood that converting a system that relies on spectral domain processing to one that relies on wavelet space processing would require significant and fundamental modifications to the system in order to accommodate the wavelet space processing (e.g., to derive a representative energy value for a signal or part of a signal requires integrating twice, across time and scale, in the wavelet domain while, conversely, one integration across frequency is required to derive a representative energy value from a spectral domain). As a further example, to reconstruct a temporal signal requires integrating twice, across time and scale, in the wavelet domain while, conversely, one integration across frequency is required to derive a temporal signal from a spectral domain. It is well known in the art that, in addition to or as an alternative to amplitude, parameters such as energy density, modulus, phase, among others may all be generated using such transforms and that these parameters have distinctly different contexts and meanings when defined in a two-dimensional frequency coordinate system rather than a three-dimensional wavelet coordinate system. For example, the phase of a Fourier system is calculated with respect to a single origin for all frequencies while the phase for a wavelet system is unfolded into two dimensions with respect to a wavelet's location (often in time) and scale.

The energy density function of the wavelet transform, the scalogram, is defined as $$S(a,b)=|T(a,b)|^2 \qquad (10)$$

where '||' is the modulus operator. The scalogram may be rescaled for useful purposes. One common rescaling is defined as $$S_R(a, b) = \frac{|T(a, b)|^2}{a} \quad (11)$$

and is useful for defining ridges in wavelet space when, for example, the Morlet wavelet is used. Ridges are defined as the locus of points of local maxima in the plane. Any reasonable definition of a ridge may be employed in the method. Also included as a definition of a ridge herein are paths displaced from the locus of the local maxima. A ridge associated with only the locus of points of local maxima in the plane are labeled a "maxima ridge".

For implementations requiring fast numerical computation, the wavelet transform may be expressed as an approximation using Fourier transforms. Pursuant to the convolution theorem, because the wavelet transform is the cross-correlation of the signal with the wavelet function, the wavelet transform may be approximated in terms of an inverse FFT of the product of the Fourier transform of the signal and the Fourier transform of the wavelet for each required a scale and then multiplying the result by $\sqrt{a}$.

In the discussion of the technology which follows herein, the "scalogram" may be taken to include all suitable forms of rescaling including, but not limited to, the original unsealed wavelet representation, linear resealing, any power of the modulus of the wavelet transform, or any other suitable resealing. In addition, for purposes of clarity and conciseness, the term "scalogram" shall be taken to mean the wavelet transform, T(a, b) itself, or any part thereof. For example, the real part of the wavelet transform, the imaginary part of the wavelet transform, the phase of the wavelet transform, any other suitable part of the wavelet transform, or any combination thereof is intended to be conveyed by the term "scalogram".

A scale, which may be interpreted as a representative temporal period, may be converted to a characteristic frequency of the wavelet function. The characteristic frequency associated with a wavelet of arbitrary a scale is given by $$f = \frac{f_c}{a} \quad (12)$$

where $f_c$, the characteristic frequency of the mother wavelet (i.e., at a=1), becomes a scaling constant and f is the representative or characteristic frequency for the wavelet at arbitrary scale a.

Any suitable wavelet function may be used in connection with the present disclosure. One of the most commonly used complex wavelets, the Morlet wavelet, is defined as:

$$\psi(t) = \pi^{-1/4}(e^{i2\pi f_0 t} - e^{-(2\pi f_0)^2/2})e^{-t^2/2} \quad (13)$$

where $f_0$ is the central frequency of the mother wavelet. The second term in the parenthesis is known as the correction term, as it corrects for the non-zero mean of the complex sinusoid within the Gaussian window. In practice, it becomes negligible for values of $f_0 \gg 0$ and can be ignored, in which case, the Morlet wavelet can be written in a simpler form as $$\psi(t) = \frac{1}{\pi^{1/4}} e^{i2\pi f_0 t} e^{-t^2/2} \quad (14)$$

This wavelet is a complex wave within a scaled Gaussian envelope. While both definitions of the Morlet wavelet are included herein, the function of equation (14) is not strictly a wavelet as it has a non-zero mean (i.e., the zero frequency term of its corresponding energy spectrum is non-zero). However, it will be recognized by those skilled in the art that equation (14) may be used in practice with $f_0 \gg 0$ with minimal error and is included (as well as other similar near wavelet functions) in the definition of a wavelet herein. A more detailed overview of the underlying wavelet theory, including the definition of a wavelet function, can be found in the general literature. Discussed herein is how wavelet transform features may be extracted from the wavelet decomposition of signals. For example, wavelet decomposition of PPG signals may be used to provide clinically useful information within a medical device.

Figure 3B:
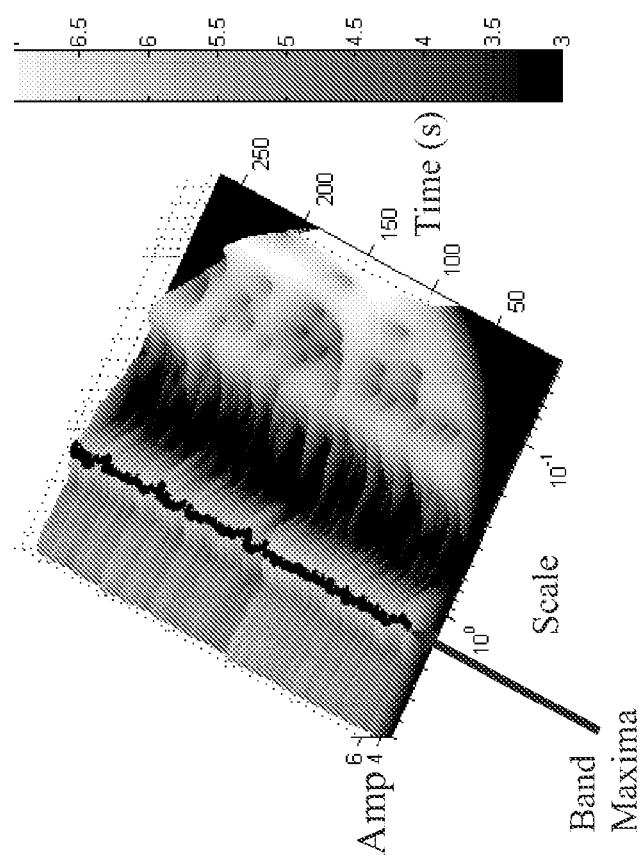
FIGS. 3(a) and 3(b) show illustrative views of a scalogram derived from a PPG signal in accordance with an embodiment.
Figure 3A:
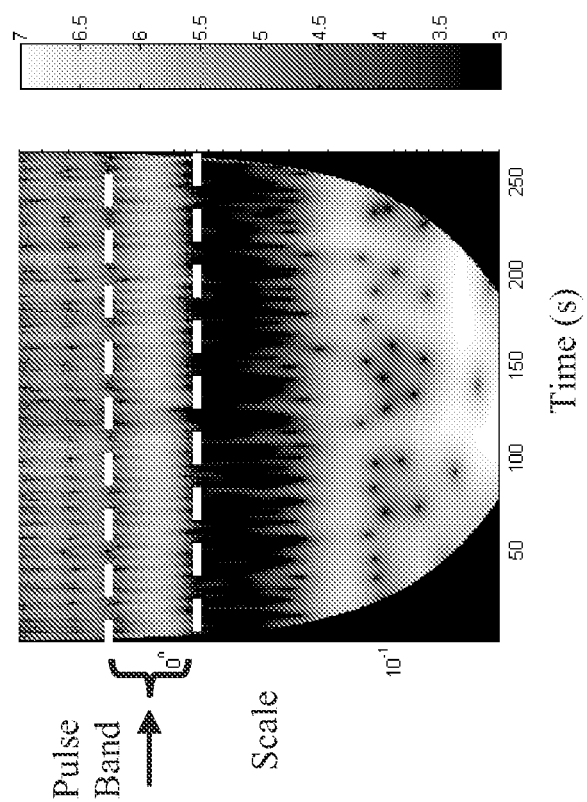

Pertinent repeating features in a signal give rise to a time-scale band in wavelet space or a resealed wavelet space. For example, the pulse component of a PPG signal produces a dominant band in wavelet space at or around the pulse frequency. FIGS. 3(a) and (b) show two views of an illustrative scalogram derived from a PPG signal, according to an embodiments. The figures show an example of the band caused by the pulse component in such a signal. The pulse band is located between the dashed lines in the plot of FIG. 3(a). The band is formed from a series of dominant coalescing features across the scalogram. This can be clearly seen as a raised band across the transform surface in FIG. 3(b) located within the region of scales indicated by the arrow in the plot (corresponding to 60 beats per minute). The maxima of this band with respect to scale is the ridge. The locus of the ridge is shown as a black curve on top of the band in FIG. 3(b). By employing a suitable resealing of the scalogram, such as that given in equation (11), the ridges found in wavelet space may be related to the instantaneous frequency of the signal. In this way, the pulse rate may be obtained from the PPG signal. Instead of resealing the scalogram, a suitable predefined relationship between the scale obtained from the ridge on the wavelet surface and the actual pulse rate may also be used to determine the pulse rate.

By mapping the time-scale coordinates of the pulse ridge onto the wavelet phase information gained through the wavelet transform, individual pulses may be captured. In this way, both times between individual pulses and the timing of components within each pulse may be monitored and used to detect heart beat anomalies, measure arterial system compliance, or perform any other suitable calculations or diagnostics. Alternative definitions of a ridge may be employed. Alternative relationships between the ridge and the pulse frequency of occurrence may be employed.

Figure 3C:
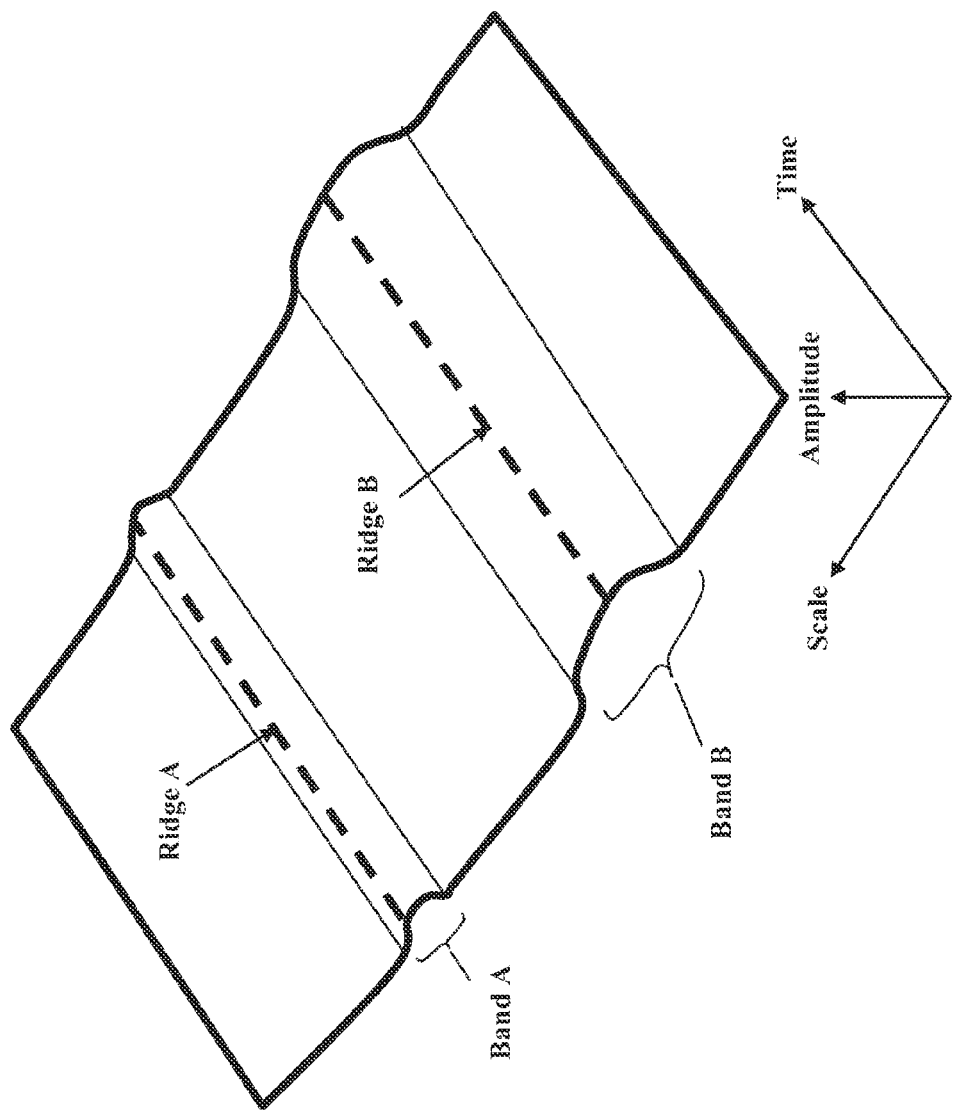
FIG. 3(c) shows an illustrative scalogram derived from a signal containing two pertinent components in accordance with an embodiment.
Figure 3D:
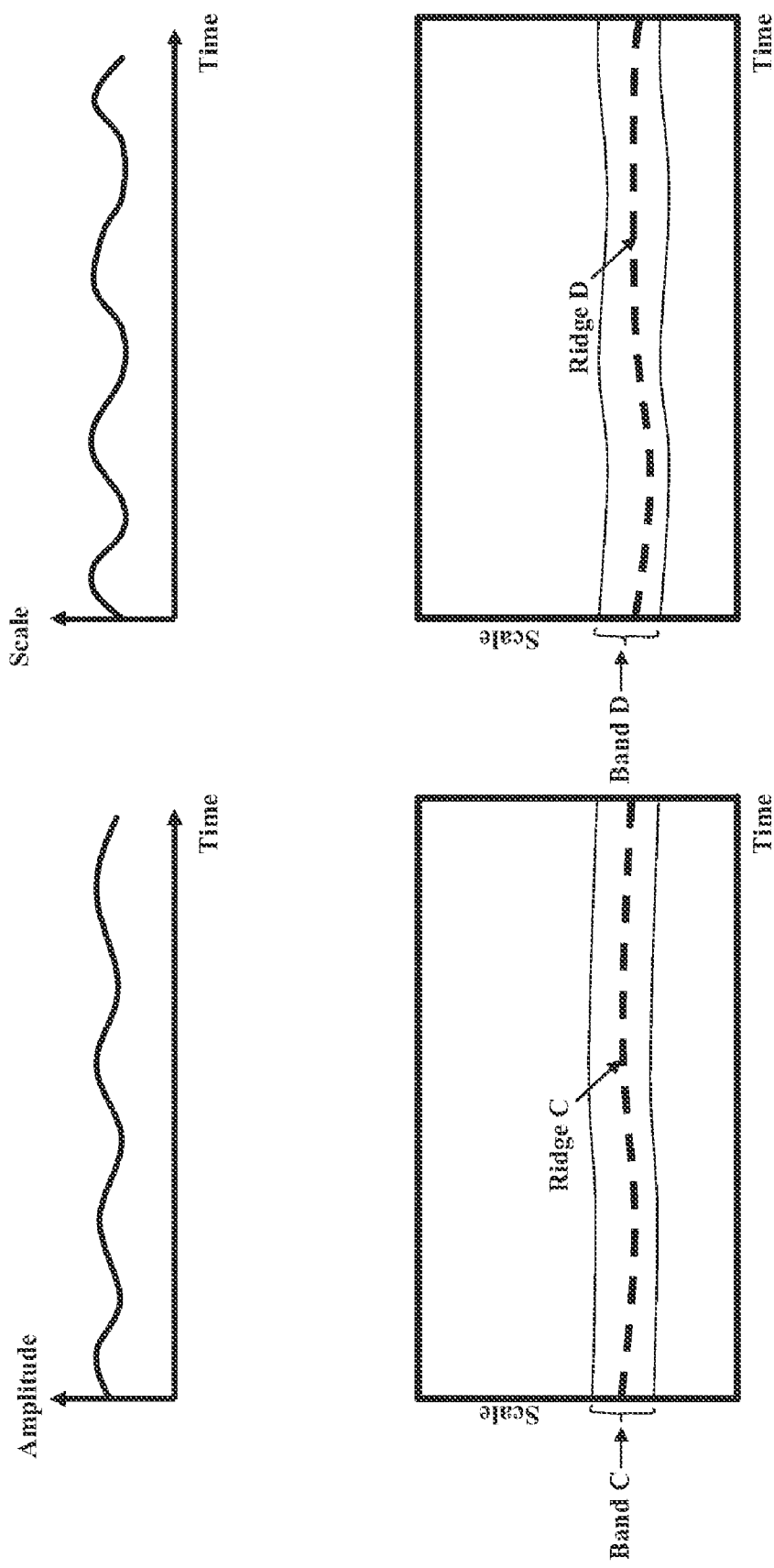
FIG. 3(d) shows an illustrative schematic of signals associated with a ridge in FIG. 3(c) and illustrative schematics of a further wavelet decomposition of these newly derived signals in accordance with an embodiment.

As discussed above, pertinent repeating features in the signal give rise to a time-scale band in wavelet space or a resealed wavelet space. For a periodic signal, this band remains at a constant scale in the time-scale plane. For many real signals, especially biological signals, the band may be non-stationary; varying in scale, amplitude, or both over time. FIG. 3(c) shows an illustrative schematic of a wavelet transform of a signal containing two pertinent components leading to two bands in the transform space, according to an embodiment. These bands are labeled band A and band B on the three-dimensional schematic of the wavelet surface. In this embodiment, the band ridge is defined as the locus of the peak values of these bands with respect to scale. For purposes of discussion, it may be assumed that band B contains the signal information of interest. This will be referred to as the "primary band". In addition, it may be assumed that the system from which the signal originates, and from which the transform is subsequently derived, exhibits some form of coupling between the signal components in band A and band B. When noise or other erroneous features are present in the signal with similar spectral characteristics of the features of band B then the information within band B can become ambiguous (i.e., obscured, fragmented or missing). In this case, the ridge of band A may be followed in wavelet space and extracted either as an amplitude signal or a scale signal which will be referred to as the "ridge amplitude perturbation" (RAP) signal and the "ridge scale perturbation" (RSP) signal, respectively. The RAP and RSP signals may be extracted by projecting the ridge onto the time-amplitude or time-scale planes, respectively. The top plots of FIG. 3(d) show a schematic of the RAP and RSP signals associated with ridge A in FIG. 3(c). Below these RAP and RSP signals are schematics of a further wavelet decomposition of these newly derived signals. This secondary wavelet decomposition allows for information in the region of band B in FIG. 3(c) to be made available as band C and band D. The ridges of bands C and D may serve as instantaneous time-scale characteristic measures of the signal components causing bands C and D. This technique, which will be referred to herein as secondary wavelet feature decoupling (SWFD), may allow information concerning the nature of the signal components associated with the underlying physical process causing the primary band B (FIG. 3(c)) to be extracted when band B itself is obscured in the presence of noise or other erroneous signal features.

In some instances, an inverse continuous wavelet transform may be desired, such as when modifications to a scalogram (or modifications to the coefficients of a transformed signal) have been made in order to, for example, remove artifacts. In one embodiment, there is an inverse continuous wavelet transform which allows the original signal to be recovered from its wavelet transform by integrating over all scales and locations, a and b:

$$x(t) = \frac{1}{C_g} \int_{-\infty}^{\infty} \int_0^{\infty} T(a,b) \frac{1}{\sqrt{a}} \psi\left(\frac{t-b}{a}\right) \frac{da\,db}{a^2} \quad (15)$$

which may also be written as:

$$x(t) = \frac{1}{C_g} \int_{-\infty}^{\infty} \int_0^{\infty} T(a,b) \psi_{a,b}(t) \frac{da\,db}{a^2} \quad (16)$$

where $C_g$ is a scalar value known as the admissibility constant. It is wavelet type dependent and may be calculated from:

$$C_g = \int_0^{\infty} \frac{|\hat{\psi}(f)|^2}{f} df \quad (17)$$

Figure 3E:
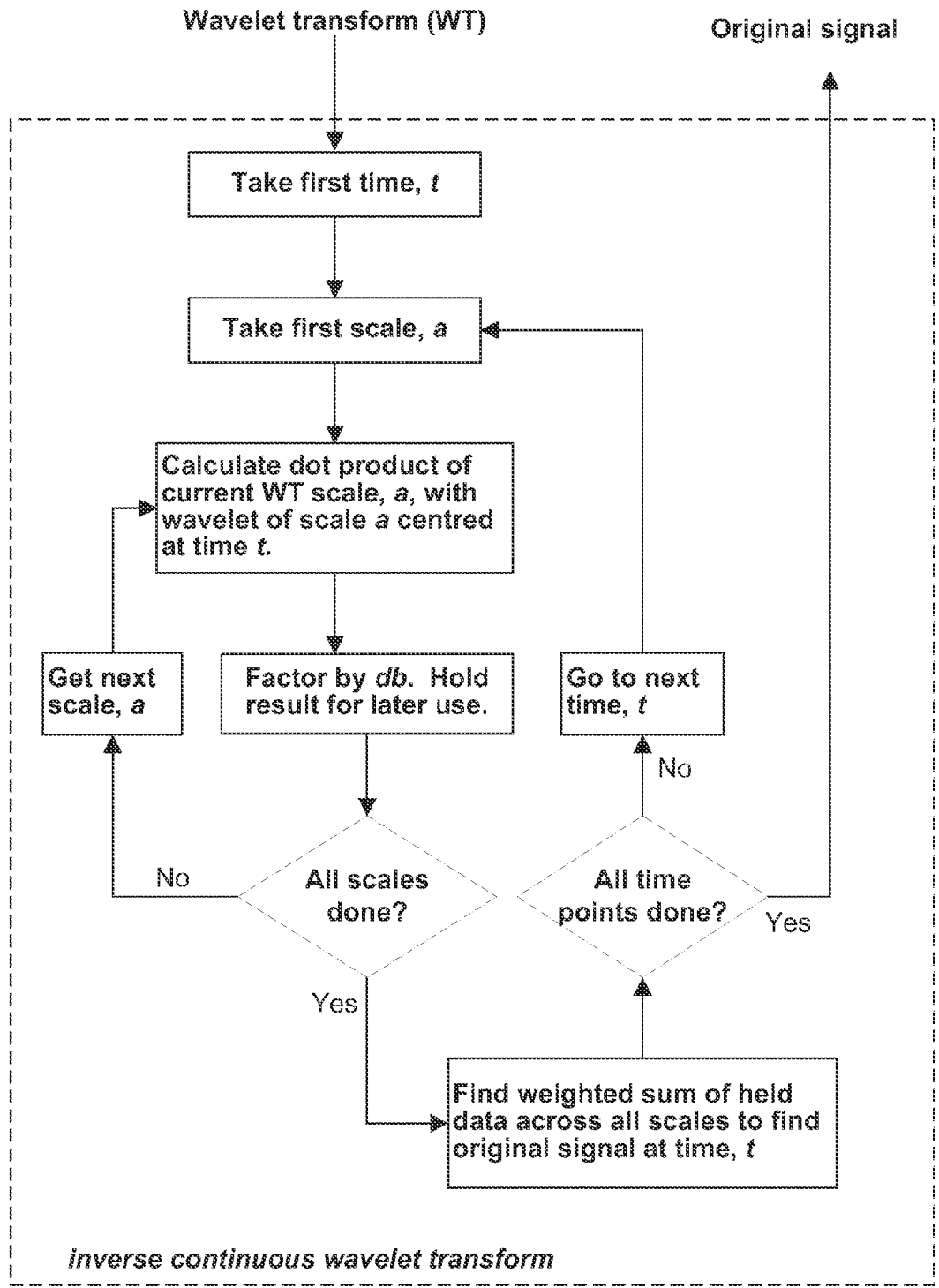
FIGS. 3(e) and 3(f) are flow charts of illustrative steps involved in performing an inverse continuous wavelet transform in accordance with embodiments.
Figure 3F:
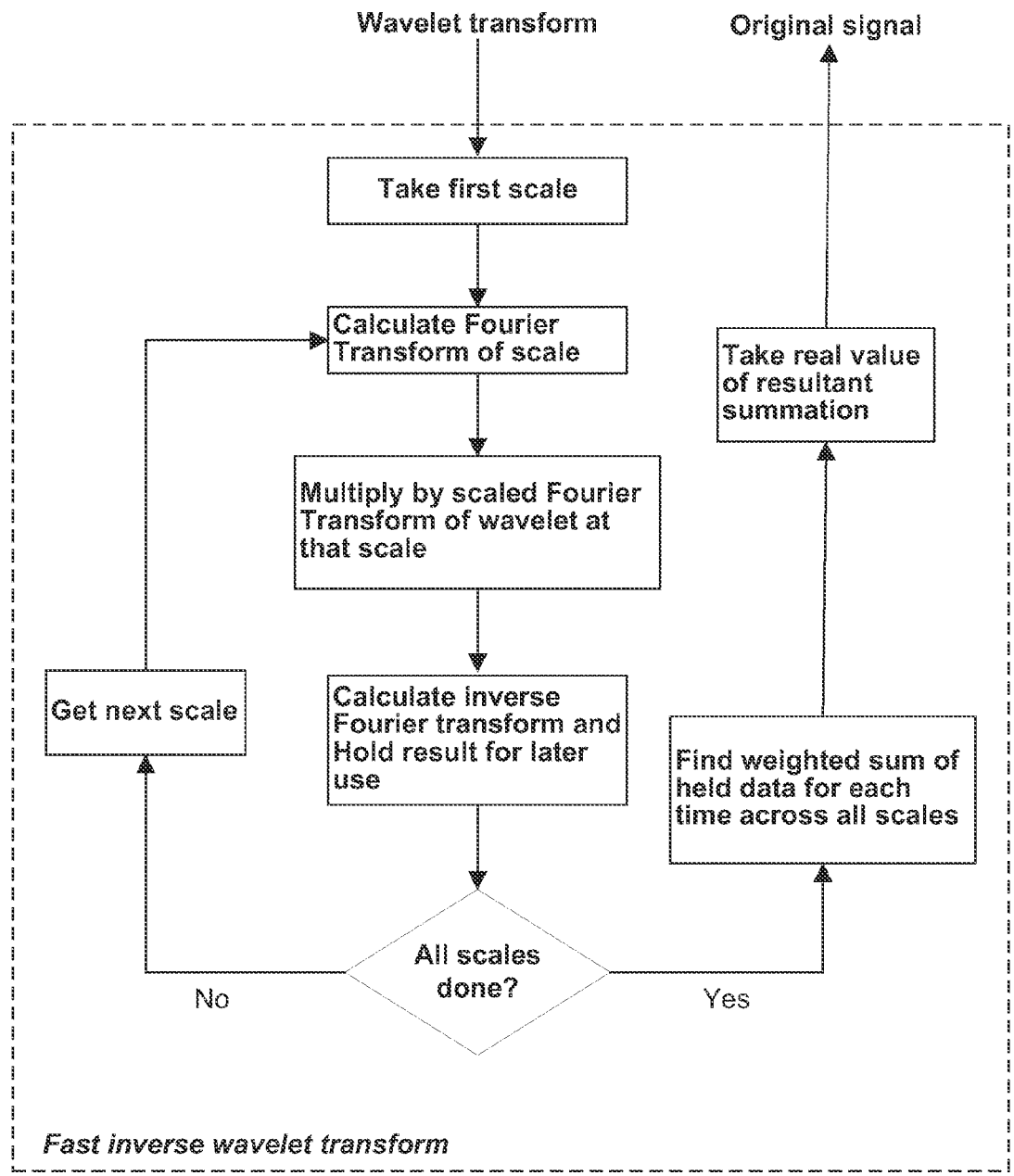

FIG. 3(e) is a flow chart of illustrative steps that may be taken to perform an inverse continuous wavelet transform in accordance with the above discussion. An approximation to the inverse transform may be made by considering equation (15) to be a series of convolutions across scales. It shall be understood that there is no complex conjugate here, unlike for the cross correlations of the forward transform. As well as integrating over all of a and b for each time t, this equation may also take advantage of the convolution theorem which allows the inverse wavelet transform to be executed using a series of multiplications. FIG. 3(f) is a flow chart of illustrative steps that may be taken to perform an approximation of an inverse continuous wavelet transform. It will be understood that any other suitable technique for performing an inverse continuous wavelet transform may be used in accordance with the present disclosure.

Figure 4:
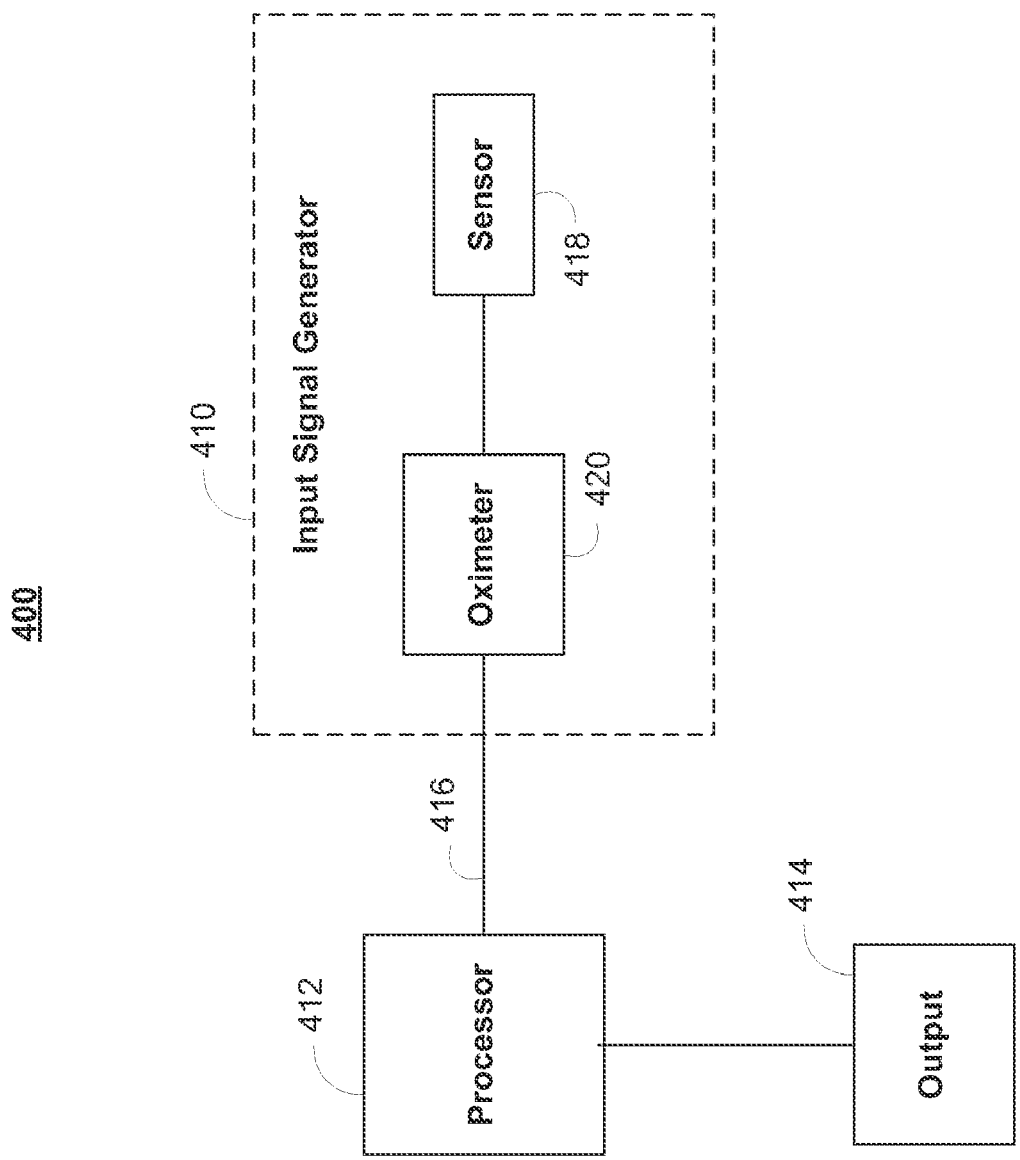
FIG. 4 is a block diagram of an illustrative continuous wavelet processing system in accordance with some embodiments.

FIG. 4 is an illustrative continuous wavelet processing system in accordance with an embodiment. In this embodiment, input signal generator 410 generates an input signal 416. As illustrated, input signal generator 410 may include oximeter 420 coupled to sensor 418, which may provide as input signal 416, a PPG signal. It will be understood that input signal generator 410 may include any suitable signal source, signal generating data, signal generating equipment, or any combination thereof to produce signal 416. Signal 416 may be any suitable signal or signals, such as, for example, biosignals (e.g., electrocardiogram, electroencephalogram, electrogastrogram, electromyogram, heart rate signals, pathological sounds, ultrasound, or any other suitable biosignal), dynamic signals, non-destructive testing signals, condition monitoring signals, fluid signals, geophysical signals, astronomical signals, electrical signals, financial signals including financial indices, sound and speech signals, chemical signals, meteorological signals including climate signals, and/or any other suitable signal, and/or any combination thereof.

In this embodiment, signal 416 may be coupled to processor 412. Processor 412 may be any suitable software, firmware, and/or hardware, and/or combinations thereof for processing signal 416. For example, processor 412 may include one or more hardware processors (e.g., integrated circuits), one or more software modules, computer-readable media such as memory, firmware, or any combination thereof. Processor 412 may, for example, be a computer or may be one or more chips (i.e., integrated circuits). Processor 412 may perform the calculations associated with the continuous wavelet transforms of the present disclosure as well as the calculations associated with any suitable interrogations of the transforms. Processor 412 may perform any suitable signal processing of signal 416 to filter signal 416, such as any suitable band-pass filtering, adaptive filtering, closed-loop filtering, and/or any other suitable filtering, and/or any combination thereof.

Processor 412 may be coupled to one or more memory devices (not shown) or incorporate one or more memory devices such as any suitable volatile memory device (e.g., RAM, registers, etch), non-volatile memory device (e.g., ROM, EPROM, magnetic storage device, optical storage device, flash memory, etc.), or both. The memory may be used by processor 412 to, for example, store data corresponding to a continuous wavelet transform of input signal 416, such as data representing a scalogram. In one embodiment, data representing a scalogram may be stored in RAM or memory internal to processor 412 as any suitable three-dimensional data structure such as a three-dimensional array that represents the scalogram as energy levels in a time-scale plane. Any other suitable data structure may be used to store data representing a scalogram.

Processor 412 may be coupled to output 414. Output 414 may be any suitable output device such as, for example, one or more medical devices (e.g., a medical monitor that displays various physiological parameters, a medical alarm, or any other suitable medical device that either displays physiological parameters or uses the output of processor 412 as an input), one or more display devices (e.g., monitor, PDA, mobile phone, any other suitable display device, or any combination thereof), one or more audio devices, one or more memory devices (e.g., hard disk drive, flash memory, RAM, optical disk, any other suitable memory device, or any combination thereof), one or more printing devices, any other suitable output device, or any combination thereof.

It will be understood that system 400 may be incorporated into system 10 (FIGS. 1 and 2) in which, for example, input signal generator 410 may be implemented as parts of sensor 12 and monitor 14 and processor 412 may be implemented as part of monitor 14.

The components and methods described herein may be used to generate one or more scalograms using a wavelet transform as described above or any other suitable method. Characteristics of the generated scalograms may be identified and used for, among other things, identifying a condition of a patient, such as a low perfusion condition, high vascular peripheral resistance, or other condition. When such conditions are identified, an alert or other event may be triggered.

A scalogram derived from a healthy individual in a steady state condition may have a dominant pulse band with low amplitudes adjacent to the pulse band. FIG. 3(*c*), which is discussed above, shows an illustrative scalogram of a signal. If a PPG signal were used to generate the scalogram in FIG. 3(*c*), band A may be the pulse band and band B may be the respiration band. Pulse band A in FIG. 3(*c*) is an example of a dominant band with low amplitudes adjacent to the pulse band.

A scalogram derived from a person that may be experiencing a medical condition or problem, such as low perfusion, may have different characteristics than a scalogram derived from a person who is not experiencing such a condition or problem. A low perfusion condition, which may be caused by increased vascular peripheral resistance, may cause changes in blood flow and pulse rates that may be detected in the scalogram. For example, a low perfusion condition may cause regions adjacent to the pulse band (e.g., above, below, or both above and below the pulse band) to contain relatively higher energy as the pulse signal becomes weaker. These regions may be referred to as marker regions. The marker regions may be spaced apart from the pulse band or may be an extension of the pulse band. Consecutive marker regions on the scalogram may be evenly spaced apart in time, randomly spaced apart in time, or the spacing may change over time. The marker regions may have any suitable shape such as, for example, rectangular, oval, square, circular, triangular, or a combination of shapes. In one example, the marker regions may be narrower in time, and longer in scale.

The marker regions may be identified in a scalogram using any suitable technique. In general, a scalogram is generated by a processor, such as processor 412 (FIG. 4) or microprocessor 48 (FIG. 2), based on signal data received from an oximeter (such as oximeter 14 (FIG. 1) or 420 (FIG. 4)) or a sensor (such as a sensor 418 (FIG. 4) or sensor 12 (FIG. 1)) that is located on a patient. The marker regions may be identified using the processor 412 (FIG. 4) or microprocessor 48 (FIG. 2) by analyzing the scalogram, as further described herein. In an embodiment, the marker regions and their sizes and shapes may be identified by the processor 412 (FIG. 4) or microprocessor 48 (FIG. 2) using an amplitude threshold. The amplitude threshold may be predetermined or may dynamically change (e.g., as a function of the height and/or shape of the pulse band). The threshold may be selected by a user (e.g., via user input 56 (FIG. 2)), or programmed for the processor 412 (FIG. 4) or microprocessor 48 (FIG. 2), and may be based in part on patient information, such as patient classification. In another embodiment, the marker regions may be identified by the processor 412 (FIG. 4) or microprocessor 48 (FIG. 2), other component, or user, based on a change in energy within one or more regions in the scalogram over time. For example, a rectangular region may be used and the energy within the region may be determined using any suitable methods such as by taking a median or average amplitude within the region or summing the amplitudes within the region. For example, a percentile of energies in a region may be used to provide a measure of background noise for comparison with the pulse band. A marker region may also be identified by the processor 412 (FIG. 4) or microprocessor 48 (FIG. 2) based on an increase and subsequent decrease in energy within the region over time. The marker regions may also be identified by using a combination of techniques by the processor 412 (FIG. 4) or microprocessor 48 (FIG. 2) or other component.

A low perfusion condition may also result in a signal that causes the amplitudes in marker regions above and below the pulse band to increase. Changes in these amplitudes may be detected and categorized by the processor 412 (FIG. 4) or microprocessor 48 (FIG. 2). In an embodiment, the amplitudes may be detected by analyzing a defined region above and/or below the pulse band over time. The defined region may be defined by the processor 412 (FIG. 4) based on one or more features of the scalogram, selected by a user (via user input 56 (FIG. 2)) or programmed in processor 412 (FIG. 4). The region may be analyzed by calculating the energy within the region or by using any other suitable technique. A low perfusion condition may also cause the amplitude of the pulse band to decrease. Any decrease in pulse band amplitude may be detected and analyzed over time by the processor 412 (FIG. 4) or microprocessor 48 (FIG. 2).

Figure 5:
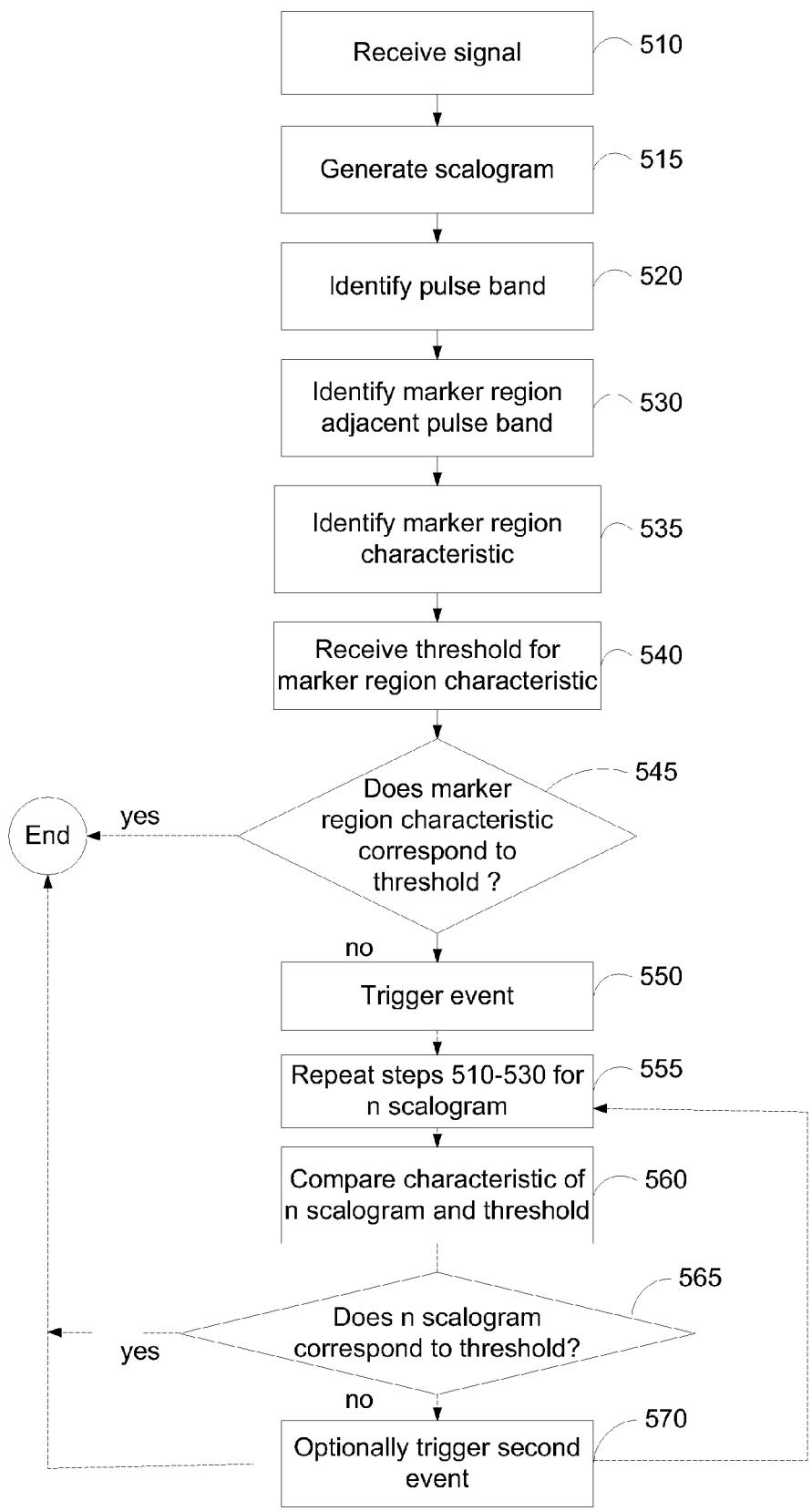
FIG. 5 shows an illustrative method for identifying a low perfusion condition in accordance with an embodiment.

FIG. 5 is an illustrative method for identifying a low perfusion condition, or other condition, according to an embodiment. At step 510, one or more signals may be received by the processor 412 (FIG. 4) or microprocessor 48 (FIG. 2). The received signal may be a PPG signal (e.g., a red and/or infrared signal), or other signal described herein, which may be transmitted by an oximeter (such as oximeter 14 of FIG. 1 or 420 of FIG. 4), sensor (such as sensor 418 of FIG. 4 or sensor 12 of FIG. 1), or other device, and may be transmitted directly (via cables 24 (FIG. 1)) to a processor (412 (FIG. 4) or microprocessor 48 (FIG. 2)), via an intermediary component, or using any appropriate transmission means. At step 515, the received signal may be used by the processor 412 (FIG. 4) or microprocessor 48 (FIG. 2) to generate a scalogram using a wavelet transform (e.g., a continuous wavelet transform), or other technique described herein or known to one of skill in the art. The scalogram may be any scalogram, such as the scalograms depicted in FIGS. 3(*a*)-(*b*) and FIG. 6(*a*).

FIGS. 6(*a*)-(*c*) depict an example of a weakening pulse signal, which may be observed in the signal plot above the scalogram of FIG. 6(*a*) and in the scalogram of FIG. 6(*a*) which shows regions adjacent to a pulse band (A) that contain relatively higher energy (B) in proportion to the pulse band (A) as the pulse signal weakens, for example in a low perfusion condition. As shown, FIG. 6(*a*) depicts a scalogram for a signal (shown at the top of the scalogram) where the pulse signal weakens. A pulse signal may weaken because of a change in a physiological condition, such as low perfusion. It may also weaken if a sensor (such as sensor 418 (FIG. 4) or sensor 12 (FIG. 1)) is moved from one location to another less optimal location, or if the sensor is loosened. Weakening a pulse signal in such ways may cause a pulse signal to reduce in amplitude. Other system noise (such as a mains hum, thermal noise, or other noise), however, typically remains constant.

The scalogram depicted in FIG. 6(*a*) may be generated based on the plotted pulse signal of FIG. 6(*a*) using techniques described herein and analyzed using techniques described herein, such as those discussed in connection with FIG. 5. The pulse signal may manifest itself in the associated wavelet scalogram as a pulse band (a distinct band across the transform plane) (marked A). Mains noise (or other noise) may manifest itself as one or more streaks (or other shape) across the scalogram at higher frequencies (marked B in the scalogram). Low amplitude signal noise from, for example, thermal noise, may be present in one or more locations in the scalogram at low energy values.

In one embodiment, in order to quantify a relative value of signal and noise, a marker region defined as a window that may be ten seconds long (or other time period), and of various widths was scanned across the scalogram and representative energies computed as described below in connection with FIGS. 6(b) and 6(c).

Figure 6A:
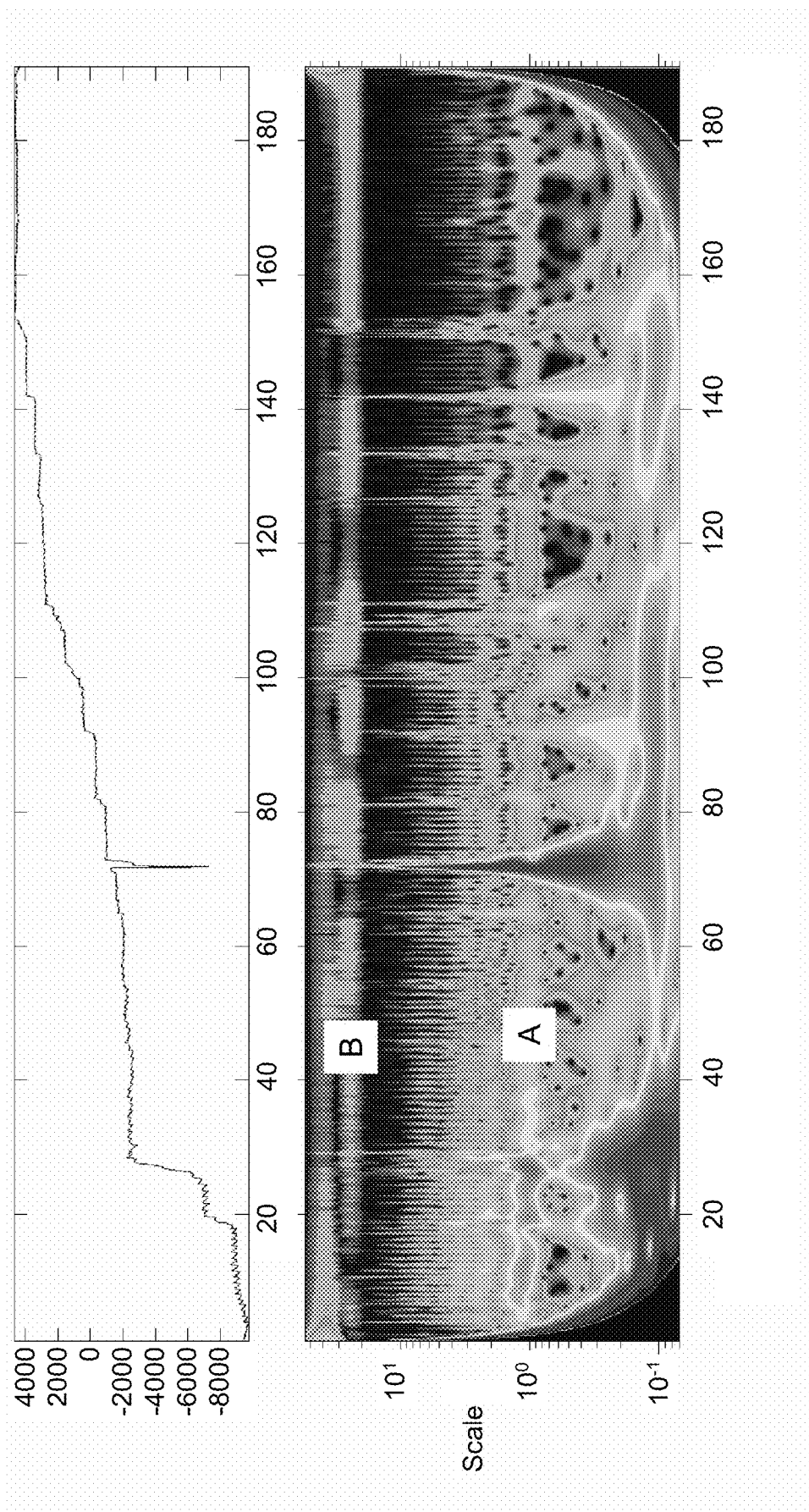
FIG. 6(a) shows a plot of a pulse signal and scalogram in accordance with an embodiment.
Figure 6B:
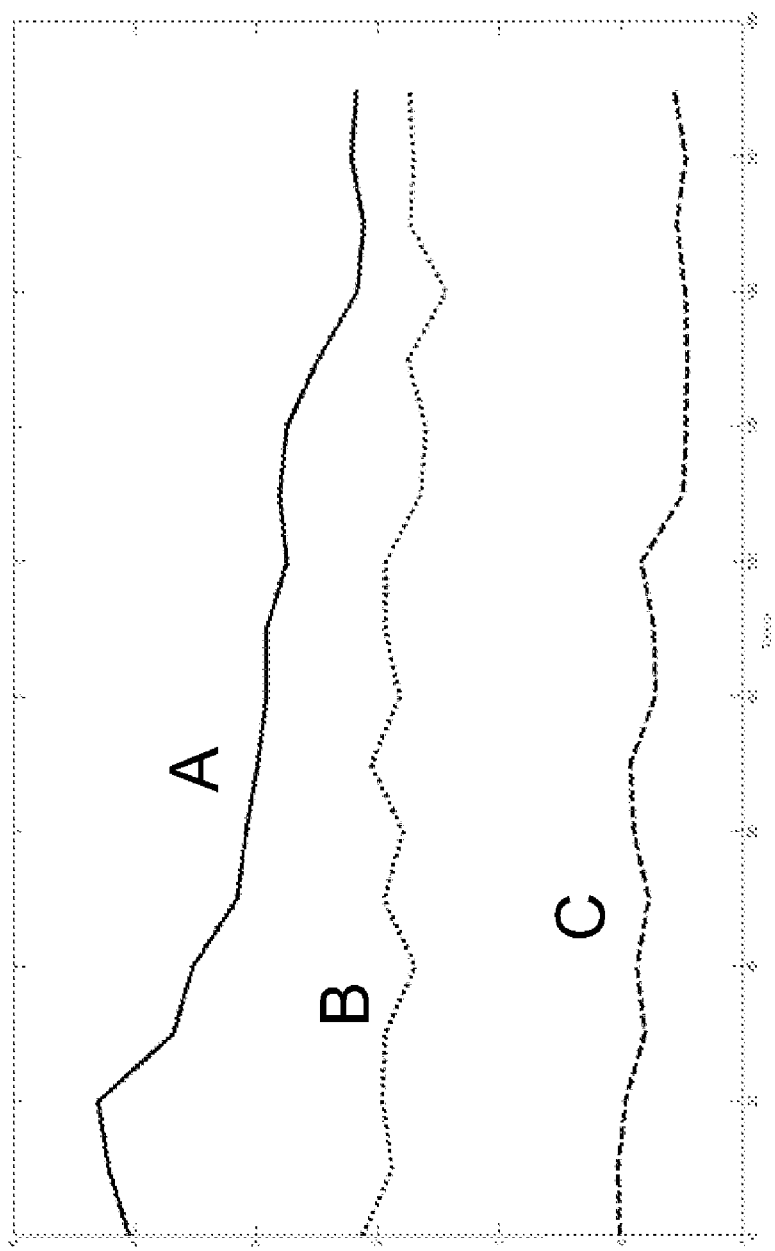
FIG. 6(b) shows a plot of energy density in accordance with an embodiment.

FIG. 6(b) shows: (1) a sum of energy densities within a ten second window localized to scales in a region of the pulse band (line A of FIG. 6(b)), (2) a sum of energy densities within a 10 second window localized to scales in the region of a mains hum artifact (line B of FIG. 6(b)) and (3) the lowest tenth percentile of energy values in the ten second window run across a region between the mains hum artifact and the pulse band (line C of FIG. 6(b)). The tenth percentile may be taken as a marker region characteristic. In one embodiment, other measures (marker region characteristics) or identifiable features (residual markers) may be interrogated or used. The plots shown in FIG. 6(b) may be produced using one or more processors, such as 412 (FIG. 4) or microprocessor 48 (FIG. 2).

Figure 6C:
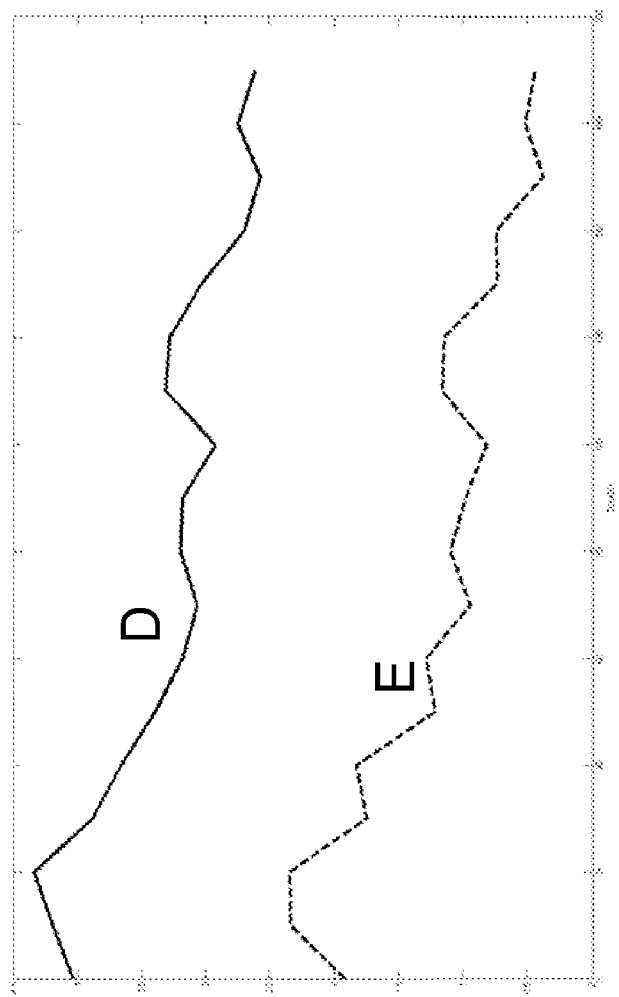
FIG. 6(c) shows a plot of representative energy in accordance with an embodiment.

To derive a measure of a pulse signal and noise levels, a pulse band's representative energy may be divided by a mains noise representative energy (line D in FIG. 6(c)), and the pulse band's representative energy may also be divided by the representative energy of low level noise (line E of FIG. 6(c)). Both of lines D and E show a decreasing trend indicative of the signal reducing relative to background noise. Such a decreasing trend may be parameterized through, for example, curve fitting, including a linear straight line fit or a nonlinear curve fit. In this way a measure of the signal quality may be obtained using wavelet transforms. This measure may be an absolute measure, a relative measure or an indication of trending over time. The plots shown in FIG. 6(c) may be produced using one or more processors, such as 412 (FIG. 4) or microprocessor 48 (FIG. 2).

Embodiments of the measures, processing, and calculations described with reference to FIGS. 6(a)-(c) may also be provided using any suitable percentiles, window lengths, and widths, to derive representative energies Representative energies may be derived in other ways such as taking a peak value in time along a pulse band maximum (i.e. its ridge). In addition, other parts of a transform may be taken or used, such as a real part, imaginary part, various powers of the modulus, and the phase.

Figure 6D:
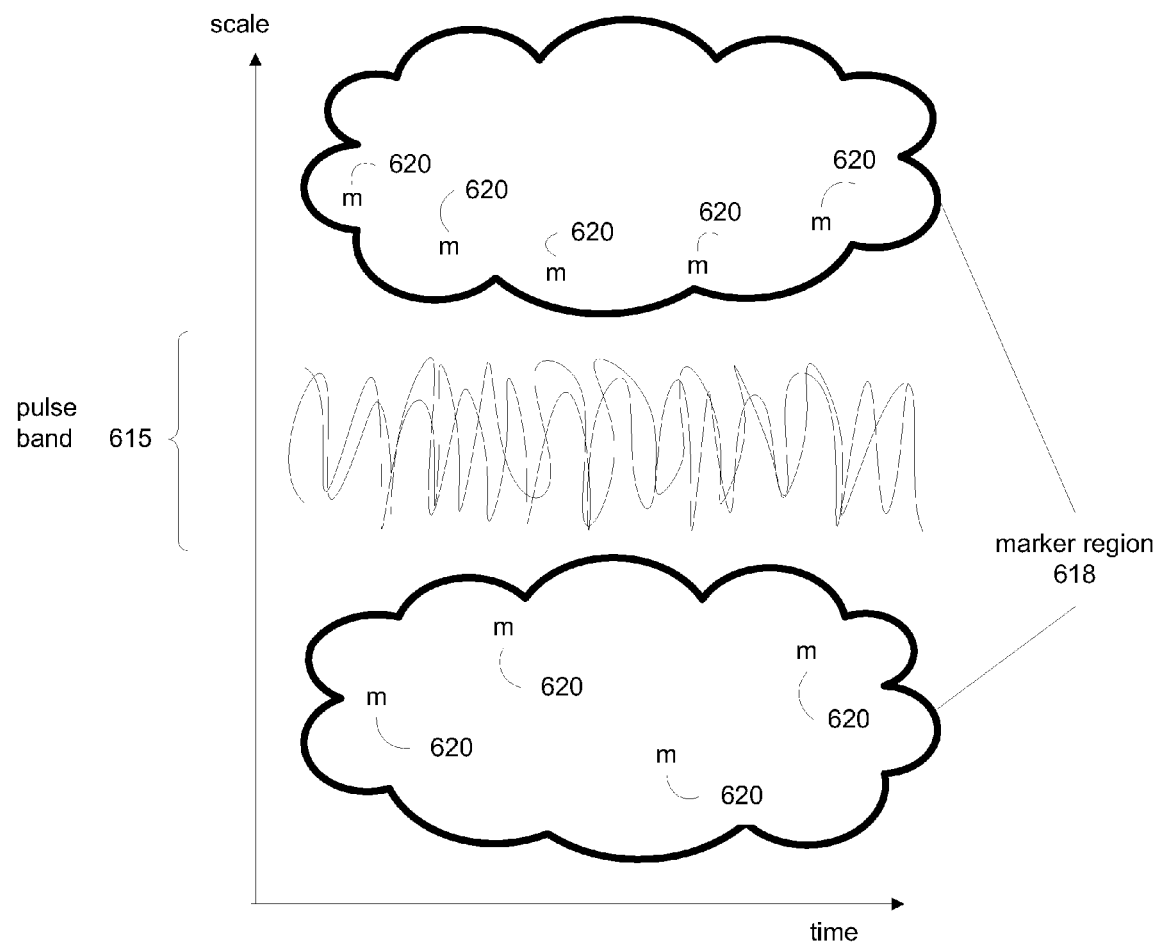
FIG. 6(d) shows an illustrative scalogram derived from a PPG signal in accordance with an embodiment.

Another exemplary simplified scalogram is depicted in FIG. 6(d). FIG. 6(d) shows a simplified scalogram 600 derived from a PPG signal. Scalogram 600 depicts pulse band 615, marker regions 618 adjacent to the pulse band 615, and residual markers 620 on either side of pulse band 615. For simplicity, scalogram 600 does not depict other features typically found in a scalogram of a PPG signal (e.g., the respiration band, noise, etc.). The scalogram 600 may be generated during a low perfusion condition. Characteristics of the residual markers 620 may be detected and analyzed by the processor 412 (FIG. 4) or microprocessor 48 (FIG. 2) to determine that there is a low perfusion condition.

Turning again to FIG. 5, at step 520, the scalogram pulse band may be identified. The pulse band may be identified by the processor (412 (FIG. 4) or microprocessor 48 (FIG. 2)) based at least in part on the scalogram data and/or the received signal from the oximeter (14 (FIG. 1) or 420 (FIG. 4)) or sensor (418 (FIG. 4) or 12 (FIG. 1)). For example, the pulse band may be identified using ridge following techniques on the scalogram, or via input for a pulse rate or interbeat time periods to locate pulse in the scalogram, or other appropriate technique. At step 530, the processor (412 (FIG. 4) or microprocessor 48 (FIG. 2)) or other component may also be used to detect one or more marker regions adjacent to the pulse band. The marker regions may be identified by the processor (412 (FIG. 4) or microprocessor 48 (FIG. 2)) using, for example, ridge or modulus maxima techniques, or other techniques well known to those skilled in the art. Marker regions may also be a defined region set forth by a user.

Characteristics of the marker region may be identified at step 535 using the processor (412 (FIG. 4) or microprocessor 48 (FIG. 2)). Some examples of characteristics of marker regions include, for example, residual markers that may be detected adjacent to the pulse band, spaced apart from the pulse band, or as an extension of the pulse band, changes in the pulse band and/or the marker regions. Residual markers may be isolated regions or may be a continuous region having increased or decreased amplitude. The size, shape, location, and amplitude of the residual markers may be determined by the processor (412 (FIG. 4) or microprocessor 48 (FIG. 2)) based on the scalogram data. A residual marker may be an identifiable feature in a marker region. Marker regions are typically regions of arbitrary shape above and/or below the pulse band. Marker region characteristics may describe characteristic measures such as a $10^{th}$ percentile (or other percentile) of energy, for example, as used in the example of FIGS. 6(a)-(c).

Figure 7:
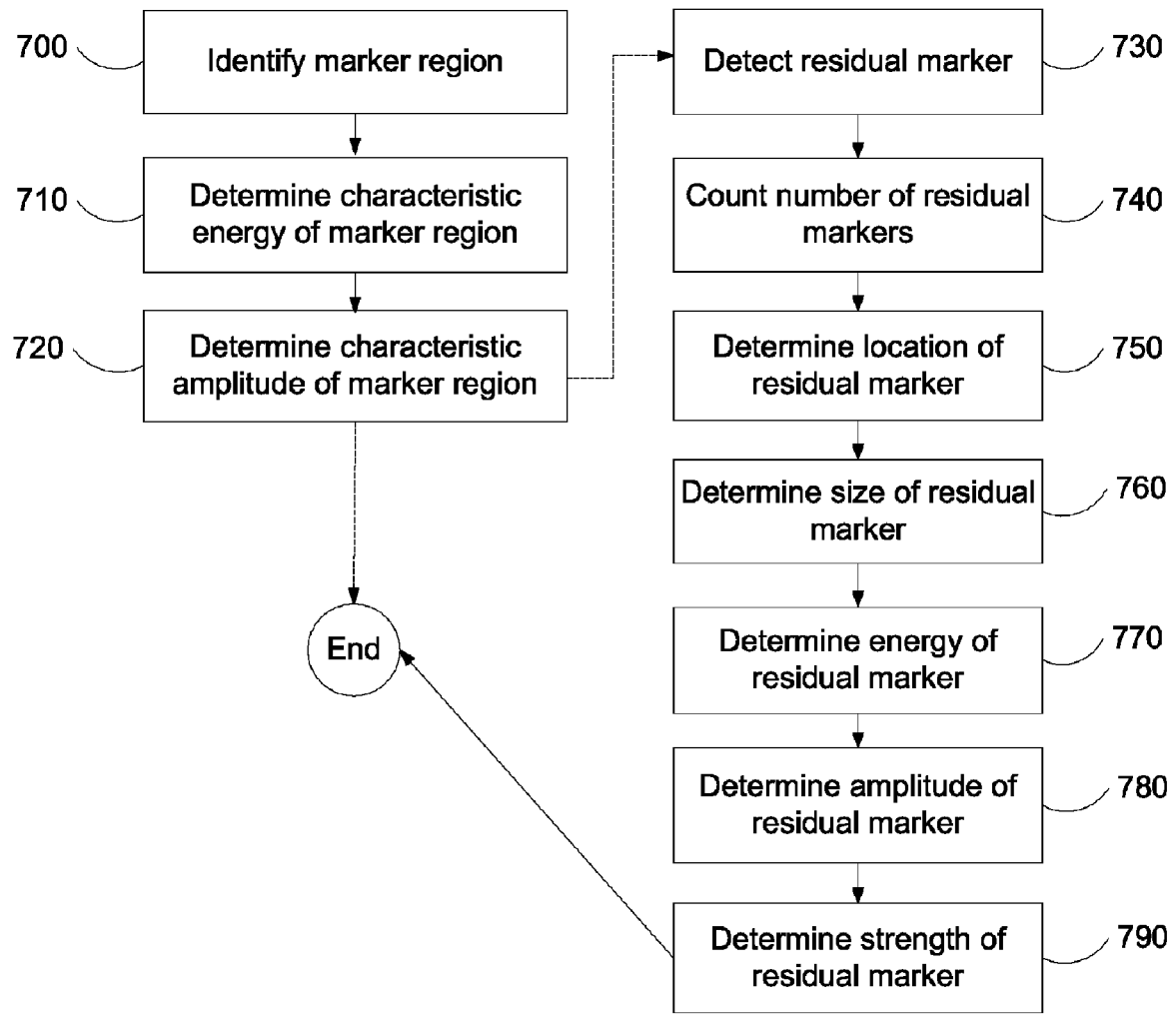
FIG. 7 shows an illustrative method for identifying a characteristic of a marker region in accordance with an embodiment.

Characteristics of the marker regions may also be identified according to the process flowchart depicted in FIG. 7. At step 700, a marker region may be identified in a manner similar to that described at step 530 (FIG. 5). The marker region may be identified using the processor (412 (FIG. 4) or microprocessor 48 (FIG. 2)) via ridge or modulus maxima techniques, or other techniques well known to those skilled in the art. In some embodiments, marker regions may be a user-defined region. Identifying characteristics of the marker region include, for example, determining energy of the marker region at step 710 and determining amplitude of the marker region at step 720. The energy and amplitude of the marker region may be obtained by processing scalogram data via processor 412 (FIG. 4) or microprocessor 48 (FIG. 2).

In some embodiments, residual markers may also be detected at step 730. The residual markers may also be detected by processor 412 (FIG. 4) or microprocessor 48 (FIG. 2) using ridge or modulus maxima techniques, or other techniques. Certain features of the residual markers may also be detected by the processor 412 (FIG. 4) or microprocessor 48 (FIG. 2), such as counting a number of residual markers at step 740, determining a location of the residual markers at step 750, determining a size of the residual markers at step 760, determining energy of the residual markers at step 770, determining amplitude of the residual markers at step 780, and determining the strength of the residual markers at step 790.

Referring again to FIG. 5, at step 540 a threshold for marker region characteristics may be received. The threshold may be selected by a user using user input 56 (FIG. 2) (or other input means), or programmed in processor 412 (FIG. 4) or microprocessor 48 (FIG. 2). The processor 412 (FIG. 4) or microprocessor 48 (FIG. 2) may determine whether the marker region characteristics correspond to the threshold at step 545. The threshold may be any combination of characteristics of the marker regions and residual markers. The number and characteristics of residual markers caused by low perfusion may vary for different people or different groups or classes of people. Therefore, thresholds used to provide an indication of low perfusion may also vary for different people, groups or classes of people. Accordingly, in an embodiment the system (via processor programming) or operator (via user inputs) may classify a patient (e.g., based on age, health condition, heart rate, body position, etc.) and the system may trigger events based at least in part on the user's classification.

The existence of residual markers (e.g., the existence of residual markers outside of the pulse band or as an extension of the pulse band) having certain characteristics has been found to indicate that the PPG signal was obtained from an oximeter (18 (FIG. 1)) or sensor (12 (FIG. 1)) located on a site having low perfusion (e.g., from high vascular peripheral resistance) or other problem. Thus, in some embodiments, if at step 545 the residual marker features are determined to not correspond to a threshold, at step 550 an event may trigger. In general, not corresponding to the threshold may include being substantially dissimilar to the threshold, exceeding or failing to meet the threshold. The event that may be triggered may be, for example, an alert or alarm that signals existence of a low perfusion condition or other condition. Other examples of alerts or events may also be triggered) for example, notifications indicating: examination of a patient is necessary, movement of the sensor is required, examination of the sensor is required, or other notification. Alerts may be of any type, such as an audible noise, lighted indicator, message, visual display, or other alarm. In addition to (or instead of) the alert, the event may be to move the sensor or oximeter (by a user operator, or using a control signal from the processor 412 (FIG. 4) sent to a wheel or roller assembly integrated in the oximeter), switch use of the sensor to a second sensor, or other event. In general, the events are triggered by the processor 412 (FIG. 4) or microprocessor 48 (FIG. 2) sending a control signal to another system component, such as displays 20 or 28 (FIG. 1), speaker 22 (FIG. 1), sensor 12 (FIG. 1), oximeter 16 (FIG. 1), or other component.

In some embodiments, steps 510-530 are repeated at step 555 as a follow up routine to determine, for example, whether the event at step 550 improved monitoring conditions. New signal information may be used to generate a new scalogram in which new marker region characteristics may be detected by the processor 412 (FIG. 4) or microprocessor 48 (FIG. 2). At step 560, the new scalogram marker region characteristics may be compared against the original scalogram and/or the threshold (received at step 540). If the new scalogram marker region characteristics correspond to the threshold at step 565, the routine may end. However, if the new scalogram marker region characteristics do not correspond to the threshold, another event may trigger at step 570. The second event may be one or more of the same or different events discussed with reference to step 555. For example, a first event triggered at step 555 may be a flashing light indicator, and a second event triggered at step 570 may be a message, audible alarm, and a flashing light. Other events, and combinations of events, may also be used. Following step 570, the system may end the routine, or optionally repeat the steps at step 555 n times.

In an embodiment, the system implementing the foregoing methods and techniques may also be used to calculate oxygen saturation. The oxygen saturation may be calculated using scalograms derived from PPG signals. For example, oxygen saturation may be calculated using the methods described in Addison et al. U.S. Patent Publication No. 2006/0258921, published Nov. 16, 2006. In an embodiment, during periods of low perfusion, the oxygen saturation may continue to be calculated using the scalograms. A reliable oxygen saturation value may continue to be calculated because low perfusion may affect scales within the scalogram without significantly affecting the pulse band. The methods and system may also be used to identify other types of conditions, as would be recognized by one of skill in the art.

The foregoing is merely illustrative of the principles of this disclosure and various modifications can be made by those skilled in the art without departing from the scope and spirit of the disclosure.

What is claimed is:

1. A method for processing a biological signal comprising:
receiving a signal at a processor;
transforming using the processer the signal using at least a wavelet transform;
generating using the processer a scalogram based at least in part on the transformed signal
identifying using the processer a pulse band in the scalogram;
identifying using the processer a marker region in the scalogram, wherein the marker region is adjacent the pulse band;
identifying using the processer a characteristic of the marker region;
determining, using the processer, based at least in part on the characteristic of the marker region and a threshold for the characteristic of the marker region, that a low perfusion condition exists; and
triggering an event.

2. The method of claim 1 wherein the signal comprises a photoplethysmograph signal from a patient.

3. The method of claim 1 wherein the marker region is positioned above or below the pulse band.

4. The method of claim 1 wherein identifying a marker region comprises using ridges or modulus maxima of the scalogram.

5. The method of claim 1 wherein the characteristic of the marker region comprises at least one of the group of: a change in energy within the marker region over time, a change in amplitude within the marker region over time, a residual marker, a number of residual markers, a size of the residual marker, a location of the residual marker, energy of the residual marker, amplitude of the residual marker, and strength of the residual marker.

6. The method of claim 1 wherein the event is triggered if the characteristic of the marker does not correspond to the threshold.

7. The method of claim 1 wherein the threshold is based in part on a user classification.

8. The method of claim 1 wherein the event is triggered based in part on a user classification.

9. The method of claim 1 wherein the event comprises one of the group of: sending a control signal to a display, sending a control signal to a speaker, generating an alert, sending a control signal to a second sensor, and moving a sensor.

10. The method of claim 1 further comprising:
generating using the processor a second scalogram based at least in part on the signal; and
comparing using the processor at least two of: the scalogram, the second scalogram, and the threshold.

11. The method of claim 9 wherein the alert comprises one of the group of: an indication of a low perfusion condition, an indication to examine a patient, an indication to move the sensor, an indication to move the sensor closer to an artery, an indication to move the sensor away from an artery, and an indication of use of a second sensor.

* * * * *